(12) United States Patent
Sakai et al.

(10) Patent No.: US 9,119,566 B2
(45) Date of Patent: Sep. 1, 2015

(54) PRESENT-ON-BED DETERMINATION APPARATUS AND SLEEP MEASUREMENT APPARATUS

(71) Applicant: TANITA CORPORATION, Tokyo (JP)

(72) Inventors: Yoshio Sakai, Tokyo (JP); Takayuki Shiota, Tokyo (JP); Chiaki Yamaya, Tokyo (JP)

(73) Assignee: TANITA CORPORATION, Tokyo (JP)

( * ) Notice: Subject to any disclaimer, the term of this patent is extended or adjusted under 35 U.S.C. 154(b) by 156 days.

(21) Appl. No.: 13/710,175

(22) Filed: Dec. 10, 2012

(65) Prior Publication Data

US 2013/0178715 A1    Jul. 11, 2013

(30) Foreign Application Priority Data

Dec. 20, 2011   (JP) ................................. 2011-277925
Jul. 9, 2012    (JP) ................................. 2012-153491

(51) Int. Cl.
*A61B 5/00* (2006.01)
*A61B 5/11* (2006.01)
*A61B 5/113* (2006.01)

(52) U.S. Cl.
CPC ............. *A61B 5/1115* (2013.01); *A61B 5/0064* (2013.01); *A61B 5/4806* (2013.01); *A61B 5/6892* (2013.01); *A61B 5/1102* (2013.01); *A61B 5/113* (2013.01); *A61B 2562/0247* (2013.01)

(58) Field of Classification Search
CPC ............................ A61B 5/6887; A61B 5/6892
USPC ................... 340/573.1, 573.4, 575, 665, 666; 600/301, 529, 532, 534, 595; 73/777, 73/862.391
See application file for complete search history.

(56) References Cited

U.S. PATENT DOCUMENTS 6,583,727 B2 *  6/2003  Nunome ....................... 340/665
6,840,907 B1 *  1/2005  Brydon ......................... 600/534
(Continued)

FOREIGN PATENT DOCUMENTS

CN    1676094 A    10/2005
CN    1718160 A    1/2006
(Continued)

OTHER PUBLICATIONS

Japanese Office Action with Full English Translation issued in Japanese Patent Application No. 2012-153491 mailed Nov. 5, 2013.
(Continued)

*Primary Examiner* — Van Trieu
(74) *Attorney, Agent, or Firm* — McDermott Will & Emery LLP

(57) ABSTRACT

A present-on-bed determination apparatus includes: a sensor unit usable with a bottom bedding and configured to measure biological displacement of a human subject on the bottom bedding so as to output a measurement signal showing a measurement result; a first signal processing unit configured to amplify the measurement signal with a first gain so as to output a first output signal; a first A/D conversion unit configured to output a plurality of first level values obtained by A/D conversion of the first output signal; and a determination unit configured to determine whether or not the human subject is present on the bottom bedding in accordance with a dispersion indicator that indicates dispersion degree of the plurality of the first level values.

26 Claims, 19 Drawing Sheets

(56) References Cited

U.S. PATENT DOCUMENTS

| | | | |
|---|---|---|---|
| 7,834,770 B2 * | 11/2010 | Kazuno | 340/573.4 |
| 8,381,336 B2 * | 2/2013 | Kazuno et al. | 5/600 |
| 2005/0234314 A1 | 10/2005 | Suzuki et al. | |
| 2006/0009704 A1 | 1/2006 | Okada et al. | |
| 2006/0169282 A1 * | 8/2006 | Izumi et al. | 128/204.23 |
| 2008/0242956 A1 * | 10/2008 | Suzuki et al. | 600/301 |
| 2009/0051550 A1 | 2/2009 | Sasaki | |
| 2013/0178715 A1 | 7/2013 | Sakai et al. | |

FOREIGN PATENT DOCUMENTS

| | | |
|---|---|---|
| CN | 203074701 U | 7/2013 |
| JP | H07-204166 A | 8/1995 |
| JP | 2004113329 A | 4/2004 |
| JP | 2006-149882 A | 6/2006 |
| JP | 2007097996 A | 4/2007 |
| JP | 2007-283030 A | 11/2007 |
| JP | 2007-285875 A | 11/2007 |
| JP | 2008-206596 | 9/2008 |
| JP | 2008-206596 A | 9/2008 |

OTHER PUBLICATIONS

Extended European Search Report issued in application No. 12194771.7-1660/ 2606822 dated Jul. 12, 2013.
Partial European Search Report issued in Application No. 12194771.7-1660 dated Mar. 18, 2013.
Chinese Office Action issued in corresponding Chinese Application No. 201210518171.4, dated May 5, 2014, with English translation.
Korean Office Action issued in corresponding Korean Application No. 10-2012-148529, dated Apr. 28, 2014, with English translation.
Korean Office Action issued in Korean Application No. 10-2012-0148529 dated Nov. 28, 2014, w/English translation.

* cited by examiner

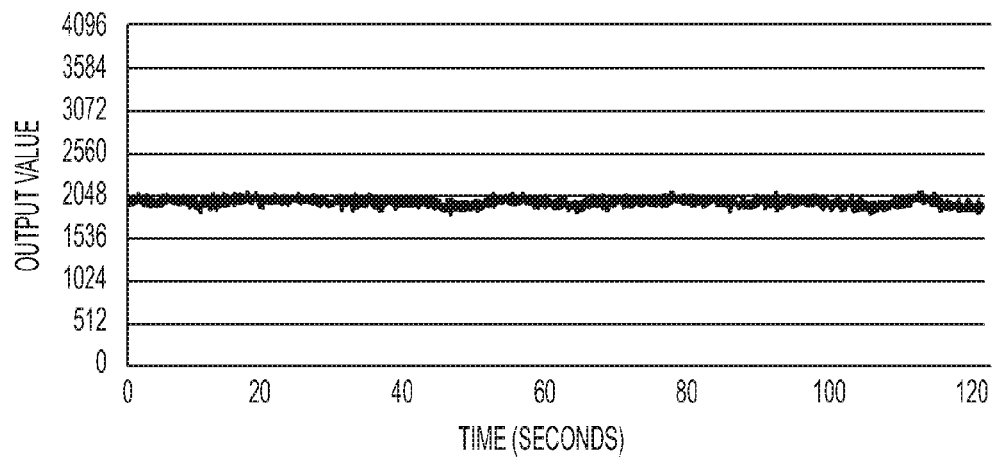
FIG. 3
FIG. 4
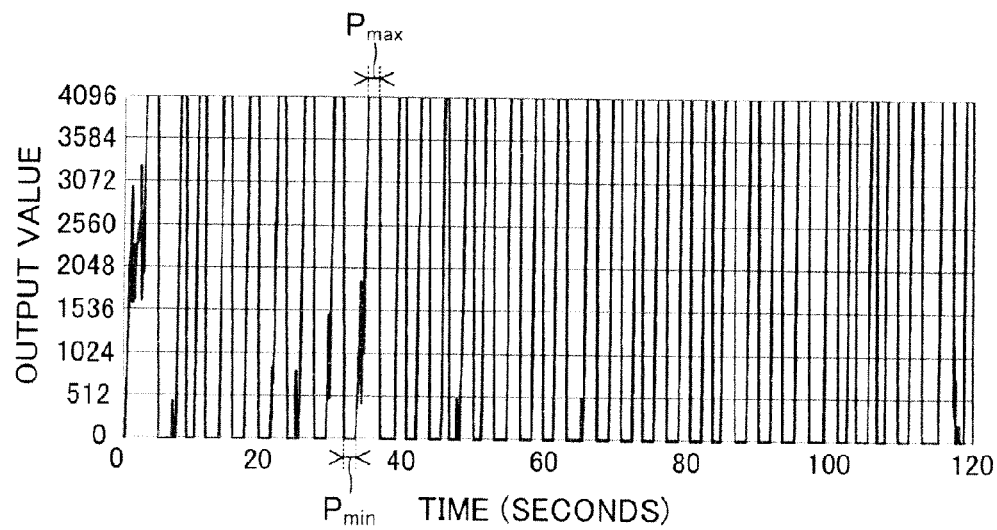

FIG. 11

| TIME t | STANDARD DEVIATION σ | PRELIMINARY DET. FLAG PF | PRESENT-ON-BED DET. FLAG LF |
|---|---|---|---|
| 50 | 51 | 0 | 0 |
| 55 | 63 | 0 | 0 |
| 60 | 879 | 1 | 0 |
| 65 | 2031 | 1 | 0 |
| 70 | 1849 | 1 | 0 |
| 75 | 1786 | 1 | 0 |
| 80 | 1986 | 1 | 1 |
| 85 | 1938 | 1 | 1 |

| TIME t | STANDARD DEVIATION σ | PRELIMINARY DET. FLAG PF | PRESENT-ON-BED DET. FLAG LF |
|---|---|---|---|
| 265 | 0 | 1 | 1 |
| 270 | 0 | 1 | 1 |
| 275 | 333 | 0 | 1 |
| 280 | 195 | 0 | 1 |
| 285 | 98 | 0 | 1 |
| 290 | 59 | 0 | 1 |
| 295 | 52 | 0 | 0 |
| 300 | 534 | 1 | 0 |
| 305 | 456 | 0 | 0 |
| 310 | 101 | 0 | 0 |

$D_{290}$, $D_{295}$, $D_{300}$

FIG. 13
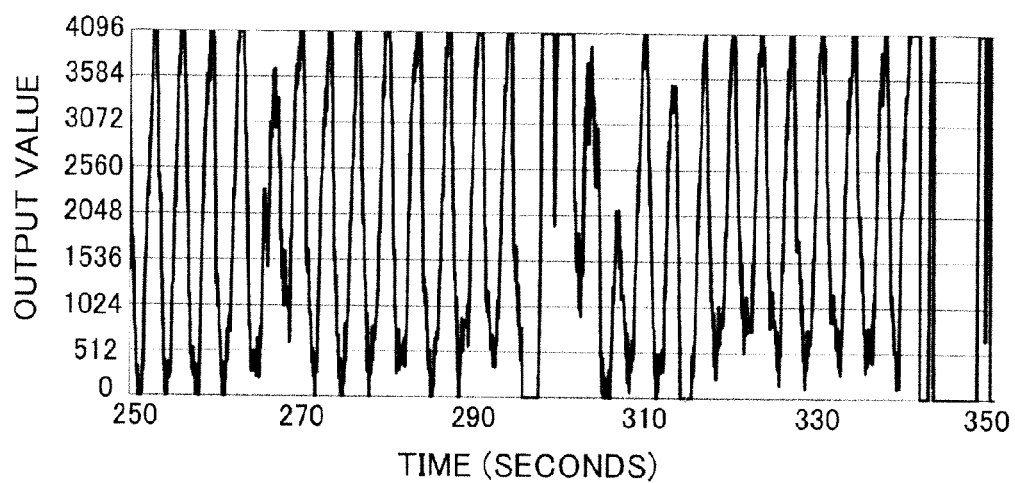
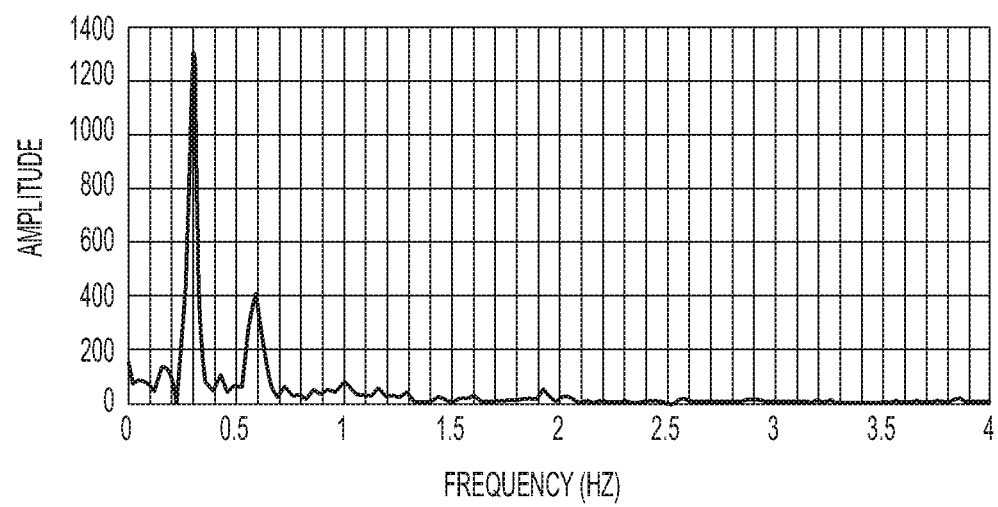
FIG. 14

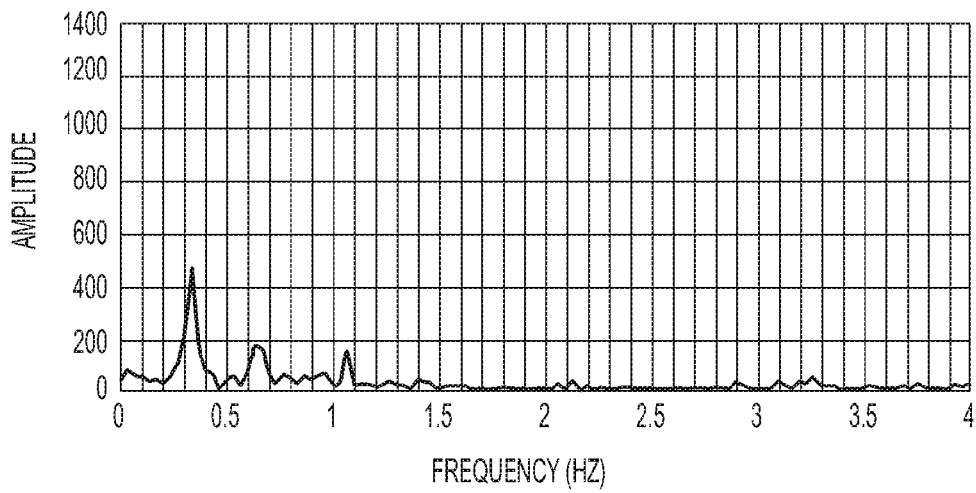
FIG. 17
FIG. 18
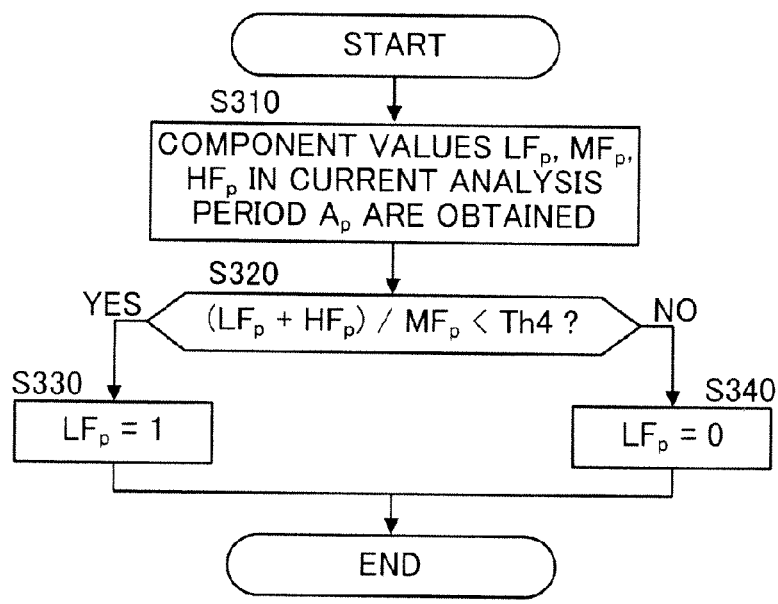

PRESENT-ON-BED DETERMINATION APPARATUS AND SLEEP MEASUREMENT APPARATUS

BACKGROUND OF THE INVENTION

1. Field of the Invention

The present invention is related to a present-on-bed determination apparatus and a sleep measurement apparatus that determine whether or not a human subject is present on a bed.

2. Related Art

In recent years, a present-on-bed determination apparatus determines whether or not a human subject is present on bottom bedding such as a mattress for bed or a Japanese-style mattress (futon) has been proposed. For instance, the present-on-bed determination apparatus may be applied to a sleep measurement apparatus that measures sleeping conditions of a human subject. The sleep measurement apparatus requires an instruction by the human subject to initiate measurement of the sleeping conditions. However, there is a problem in that the human subject tends to forget to give the instruction (e.g., to operate a button) since sleep is unremarkable behavior for him or her. The present-on-bed determination apparatus enables determining whether or not the human subject is present on a bed and to execute sleep measurement without any special operation thereof by the human object. For instance, Patent Document 1 discloses a technique to determine whether or not the human subject is present on a bed (has gone to bed) by measuring body movement of the human subject (mattress oscillation) so as to measure sleeping conditions.

Patent Document 1: Japanese Patent Application Laid-Open Publication No. 2008-206596

According to the technique of Patent Document 1, an output signal is generated from a sensor based on the mattress oscillation, and it is determined that the human subject is present on a bed if a level of the output signal exceeds a predetermined threshold. In this technique, if the mattress is subject to impact, it is likely to be determined that the human subject is present on a bed even though no one is present on the bed.

SUMMARY OF THE INVENTION

Accordingly, an object of the present invention is to enable to determine in an appropriate manner whether or not a human subject is present on a bed.

In accordance with an aspect of the present invention, a present-on-bed determination apparatus includes: a sensor unit usable with a bottom bedding and configured to measure biological displacement of a human subject on the bottom bedding so as to output a measurement signal showing a measurement result; a first signal processing unit configured to amplify the measurement signal with a first gain so as to output a first output signal; a first A/D conversion unit configured to output a plurality of first level values obtained by A/D conversion of the first output signal; and a determination unit configured to determine whether or not the human subject is present on the bottom bedding in accordance with a dispersion indicator that indicates dispersion degree of the plurality of the first level values.

In this description, "biological displacement" means physical displacement (e.g., increase and decrease of body volume) generated by biological activity such as respiration, heartbeat, or body motion of the human subject.

Another present-on-bed determination apparatus according to the present invention includes: a sensor unit usable with a bottom bedding and configured to measure biological displacement of a human subject on the bottom bedding so as to output a measurement signal showing a measurement result; a first A/D conversion unit configured to output a plurality of first sample values obtained by A/D conversion of the measurement signal; a first signal processing unit configured to numerically amplify the plurality of the first sample values with a first gain so as to output a plurality of first level values; and a determination unit configured to determine whether or not the human subject is present on the bottom bedding in accordance with a dispersion indicator that indicates dispersion degree of the plurality of the first level values.

According to these configurations, it is determined whether or not the human subject is present on the bottom bedding in accordance with the dispersion degree of the first level values that reflect the biological displacement of the human subject. Therefore, these configurations provide more accurate present-on-bed determination compared with a configuration that determines whether or not the human subject is present on a bed in accordance with only first-level-value magnitude.

Preferably, the first gain is configured so that a possible maximum value and a possible minimum value of the first level values are included in the plurality of the first level values obtained during one cycle of a periodic component contained in the biological displacement of the human subject present on the bottom bedding.

In this description, the "periodic component contained in the biological displacement" means periodic and physical displacement generated by periodic and biological activity such as respiration or heartbeat of the human subject.

In this instance, the first level values in which the human subject is present on a bed are notably different and easily distinguishable from the first level values in which the human subject is not present on a bed. Therefore, accuracy of the present-on-bed determination can be maintained in a case in which the sleep measurement apparatus is applied to various beddings (e.g., a bed or Japanese-style mattress) and various types of human subjects (e.g., a heavy person or a lightweight person).

Preferably, the determination unit determines that a preliminary condition is fulfilled if the dispersion indicator of the plurality of the first level values obtained during a predetermined period exceeds a first threshold or is equal to 0. The determination unit may also determine that the human subject is present on the bottom bedding if a number of cases in which the preliminary condition is fulfilled in n (n is a natural number equal to or greater than 2) consecutive predetermined periods is equal to or greater than a second threshold.

In this instance, it is determined that the human subject has come to be present on (or is getting into) a bed if the preliminary conditions are fulfilled with a high frequency. As a result, an erroneous determination that the human subject is present on the bed based on a temporary increase of the standard deviation of the first level values depending on noise or the like can be avoided.

Preferably, after it is determined that the human subject is present on the bottom bedding, the determination unit determines that the human subject is not present on the bottom bedding if a number of cases in which the preliminary condition is fulfilled in m (m is a natural number equal to or greater than 2) consecutive predetermined periods is equal to or less than a third threshold.

In this instance, in a case in which the human subject is present on a bed, it is determined that the human subject has come not to be present on (or leaves) the bed if the preliminary conditions are fulfilled with a low frequency. As a result, an erroneous determination that the human subject is not present on the bed based on the temporary decrease of the standard deviation of the first level values depending on noise or the like can be prevented.

Preferably, each time length of the predetermined periods is configured to be longer than a time length required for the one cycle of the periodic component.

In this instance, a single predetermined period may contain one cycle of the periodic component. If so, dispersion degree of the plurality of the first level values obtained during the predetermined period can be increased. As a result, the present-on-bed determination of the human subject can be provided with greater accuracy.

Preferably, the dispersion indicator is a standard deviation, a variance, or a variation coefficient of the plurality of the first level values obtained during the predetermined period.

Another present-on-bed determination apparatus according to the present invention includes: a sensor unit usable with a bottom bedding and configured to measure biological displacement of a human subject on the bottom bedding so as to output a measurement signal showing a measurement result; a first signal processing unit configured to amplify the measurement signal with a first gain so as to output a first output signal; a first A/D conversion unit configured to output a plurality of first level values obtained by A/D conversion of the first output signal; and a determination unit configured to execute frequency analysis on the plurality of the first level values output during an analysis period to obtain a first component not derived from the biological displacement of the human subject and a second component derived from the biological displacement of the human subject, and configured to determine whether or not the human subject is present on the bottom bedding in accordance with a ratio between the first component and the second component.

Another present-on-bed determination apparatus according to the present invention includes: a sensor unit usable with a bottom bedding and configured to measure biological displacement of a human subject on the bottom bedding so as to output a measurement signal showing a measurement result; a first A/D conversion unit configured to output a plurality of first sample values obtained by A/D conversion of the measurement signal; a first signal processing unit configured to numerically amplify the plurality of the first sample values with a first gain so as to output a plurality of first level values; and a determination unit configured to execute frequency analysis on the plurality of the first level values output during an analysis period to obtain a first component not derived from the biological displacement of the human subject and a second component derived from the biological displacement of the human subject, and configured to determine whether or not the human subject is present on the bottom bedding in accordance with a ratio between the first component and the second component.

According to these configurations, it is determined whether or not the human subject is present on the bottom bedding in accordance with the components obtained by the frequency analysis on the first level values that reflect the biological displacement of the human subject. Therefore, these configurations provide more accurate present-on-bed determination compared with a configuration that determines whether or not the human subject is present on a bed in accordance with only first-level-value magnitude.

Preferably, the determination unit obtains any one or both of a component less than a first frequency and a component greater than a second frequency that exceeds the first frequency as the first component, and obtains a component greater than the first frequency and less than the second frequency as the second component.

Preferably, the first gain is configured so that a possible maximum value and a possible minimum value of the first level values are included in the plurality of the first level values obtained during one cycle of a periodic component contained in the biological displacement of the human subject present on the bottom bedding.

In this instance, such amplification of the first level values with the first gain enables the determination unit to more certainly obtain a cyclic component included in the biological displacement.

Preferably, the ratio represents a ratio of the first component to the second component, and the determination unit determines that the human subject is present on the bottom bedding if the ratio obtained during the analysis period is less than a fourth threshold. More preferably, after it is determined that the human subject is present on the bottom bedding, the determination unit determines that the human subject is not present on the bottom bedding if the ratio obtained during an analysis period is greater than a fifth threshold.

In this instance, it is determined that the human subject is present on the bottom bedding if the ratio of the first component to the second component is less than the fourth threshold, that is, if the second component derived from the biological displacement is relatively large. It is determined that the human subject is not present on the bottom bedding if the ratio exceeds the fifth threshold, that is, if the second component is relatively small. Such present-on-bed determination based on the ratio can prevent an erroneous determination when output values (fluctuation range) of the first level values are decreased.

In accordance with another preferable aspect of the present invention, the ratio represents a ratio of the second component to the first component, and the determination unit determines that the human subject is present on the bottom bedding if the ratio obtained during the analysis period is greater than a fourth threshold. More preferably, after it is determined that the human subject is present on the bottom bedding, the determination unit determines that the human subject is not present on the bottom bedding if the ratio obtained during an analysis period is less than a fifth threshold.

In this instance, it is determined that the human subject is present on the bottom bedding if the ratio of the second component to the first component exceeds the fourth threshold, that is, if the second component derived from the biological displacement, is relatively large. It is determined that the human subject is not present on the bottom bedding if the ratio is less than the fifth threshold, that is, if the second component is relatively small. Such present-on-bed determination based on the ratio can prevent an erroneous determination when output values (fluctuation range) of the first level values are decreased.

Another present-on-bed determination apparatus according to the present invention includes: a sensor unit usable with a bottom bedding and configured to measure biological displacement of a human subject on the bottom bedding so as to output a measurement signal showing a measurement result; a first signal processing unit configured to amplify the measurement signal with a first gain so as to output a first output signal; a first A/D conversion unit configured to output a plurality of first level values obtained by A/D conversion of the first output signal; a first determination unit configured to determine whether or not the human subject is present on the bottom bedding in accordance with a dispersion indicator that indicates dispersion degree of the plurality of the first level values; and a second determination unit configured to execute frequency analysis on the plurality of the first level values output during an analysis period to obtain a first component not derived from the biological displacement of the human subject and a second component derived from the biological displacement of the human subject, and configured to determine whether or not the human subject is present on the bottom bedding in accordance with a ratio between the first component and the second component.

Another present-on-bed determination apparatus according to the present invention includes: a sensor unit usable with a bottom bedding and configured to measure biological displacement of a human subject on the bottom bedding so as to output a measurement signal showing a measurement result; a first A/D conversion unit configured to output a plurality of first sample values obtained by A/D conversion of the measurement signal; a first signal processing unit configured to numerically amplify the plurality of the first sample values with a first gain so as to output a plurality of first level values; a first determination unit configured to determine whether or not the human subject is present on the bottom bedding in accordance with a dispersion indicator that indicates dispersion degree of the plurality of the first level values; and a second determination unit configured to execute frequency analysis on the plurality of the first level values output during an analysis period to obtain a first component not derived from the biological displacement of the human subject and a second component derived from the biological displacement of the human subject, and configured to determine whether or not the human subject is present on the bottom bedding in accordance with a ratio between the first component and the second component.

According to these configurations, it is determined whether or not the human subject is present on the bottom bedding in accordance with the dispersion degree of the first level values that reflect the biological displacement of the human subject and the components obtained by the frequency analysis on the first level values. Therefore, these configurations provide more accurate present-on-bed determination compared with a configuration that determines whether or not the human subject is present on the bed in accordance with only any one of the dispersion degree of the first level values or the components obtained by the frequency analysis on the first level values.

Preferably, the second determination unit obtains any one or both of a component less than a first frequency and a component greater than a second frequency that exceeds the first frequency as the first component, and obtains a component greater than the first frequency and less than the second frequency as the second component.

Preferably, the first gain is configured so that a possible maximum value and a possible minimum value of the first level values are included in the plurality of the first level values obtained during one cycle of a periodic component contained in the biological displacement of the human subject present on the bottom bedding.

Preferably, the present-on-bed determination apparatus includes a signal generator. The first determination unit may determine that a preliminary condition is fulfilled if the dispersion indicator of the plurality of the first level values obtained during a predetermined period exceeds a first threshold or is equal to 0, and may determine that the human subject is present on the bottom bedding if a number of cases in which the preliminary condition is fulfilled in n (n is a natural number equal to or greater than 2) consecutive predetermined periods is equal to or greater than a second threshold. The ratio may represent a ratio of the first component to the second component. The second determination unit may determine that the human subject is present on the bottom bedding if the ratio obtained during the analysis period is less than a fourth threshold. The signal generator may generate a signal showing that the human subject is present on the bottom bedding in a case in which both the first determination unit and the second determination unit determine that the human subject is present on the bottom bedding.

In this instance, when the present-on-bed determination result by the first determination unit based on the dispersion indicator and the present-on-bed determination result by the second determination unit based on the frequency analysis are matched with each other, the signal showing that the human subject is present on the bottom bedding is generated.

More preferably, after the second determination unit determines that the human subject is present on the bottom bedding, the first determination unit determines that the human subject is not present on the bottom bedding if a number of cases in which the preliminary condition is fulfilled in m (m is a natural number equal to or greater than 2) consecutive predetermined periods is equal to or less than a third threshold, the second determination unit determines that the human subject is not present on the bottom bedding if the ratio obtained during an analysis period is greater than a fifth threshold, and the signal generator generates a signal showing that the human subject is not present on the bottom bedding in a case in which both the first determination unit and the second determination unit determine that the human subject is not present on the bottom bedding.

In this instance, when the present-on-bed determination result by the first determination unit based on the dispersion indicator and the present-on-bed determination result by the second determination unit based on the frequency analysis are matched with each other, the signal showing that the human subject is not present on the bottom bedding is generated.

In accordance with another preferable aspect of the present invention, the present-on-bed determination apparatus includes a signal generator. The first determination unit may determine that a preliminary condition is fulfilled if the dispersion indicator of the plurality of the first level values obtained during a predetermined period exceeds a first threshold or is equal to 0, and may determine that the human subject is present on the bottom bedding if a number of cases in which the preliminary condition is fulfilled in n (n is a natural number equal to or greater than 2) consecutive predetermined periods is equal to or greater than a second threshold. The ratio may represent a ratio of the second component to the first component. The second determination unit may determine that the human subject is present on the bottom bedding if the ratio obtained during the analysis period is greater than a fourth threshold. The signal generator may generate a signal showing that the human subject is present on the bottom bedding in a case in which both the first determination unit and the second determination unit determine that the human subject is present on the bottom bedding.

More preferably, after the second determination unit determines that the human subject is present on the bottom bedding, the first determination unit determines that the human subject is not present on the bottom bedding if a number of cases in which the preliminary condition is fulfilled in m (m is a natural number equal to or greater than 2) consecutive predetermined periods is equal to or less than a third threshold, the second determination unit determines that the human subject is not present on the bottom bedding if the ratio obtained during an analysis period is less than a fifth threshold, and the signal generator generates a signal showing that the human subject is not present on the bottom bedding in a case in which both the first determination unit and the second determination unit determine that the human subject is not present on the bottom bedding.

Preferably, each time length of the predetermined periods is configured to be longer than a time length required for the one cycle of the periodic component.

Preferably, the dispersion indicator is a standard deviation, a variance, or a variation coefficient of the plurality of the first level values obtained during the predetermined period.

In accordance with an aspect of the present invention, a sleep measurement apparatus includes: any one of the above-described present-on-bed determination apparatuses; in a case in which it is determined that the human subject is present on the bottom bedding, a second signal processing unit configured to amplify the measurement signal with a second gain less than the first gain so as to output a second output signal; a second A/D conversion unit configured to output a plurality of second level values obtained by A/D conversion of the second output signal; a biological information acquisition unit configured to obtain biological information of the human subject based on the second level values to output the biological information; and a measurement unit configured to measure sleeping conditions of the human subject based on the biological information.

Another sleep measurement apparatus according to the present invention includes: any one of the above-described present-on-bed determination apparatuses; in a case in which it is determined that the human subject is present on the bottom bedding, a second A/D conversion unit configured to output a plurality of second sample values obtained by A/D conversion of the measurement signal; a second signal processing unit configured to numerically amplify the plurality of the second sample values with a second gain less than the first gain so as to output a plurality of second level values; a biological information acquisition unit configured to obtain biological information of the human subject based on the second level values to output the biological information; and a measurement unit configured to measure sleeping conditions of the human subject based on the biological information.

In these configurations, the sleep measurement apparatus with the present-on-bed determination apparatus according to the present invention is provided. The human subject tends to forget to give instructions to initiate and terminate a sleep measurement process since sleep is an unremarkable behavior for the human subject. According to these configurations, it is automatically determined whether or not the human subject is present on a bed, so that the sleep measurement process is initiated or terminated, which provides the human subject with greater convenience.

BRIEF DESCRIPTION OF DRAWINGS

FIG. 3 illustrates an example of transition of first level values.

FIG. 4 illustrates an example of transition of first level values.

FIG. 11 shows an example of determination results according to a present-on-bed determination process according to a first embodiment of the present invention.

FIG. 12 shows an example of determination results according to a present-on-bed determination process according to a first embodiment of the present invention.

FIG. 13 illustrates an example of transition of first level values.

FIG. 14 illustrates an example of a frequency waveform obtained by frequency analysis on a time waveform of first level values.

FIG. 17 illustrates another example of a frequency waveform obtained by frequency analysis on a time waveform of first level values.

FIG. 18 is a flowchart that illustrates a present-on-bed determination operation according to a second embodiment in which the human subject is not present on the bed.

DETAILED DESCRIPTION OF PREFERRED EMBODIMENTS

First Embodiment

1. Configurations of Sleep Measurement Apparatus

Figure 1:
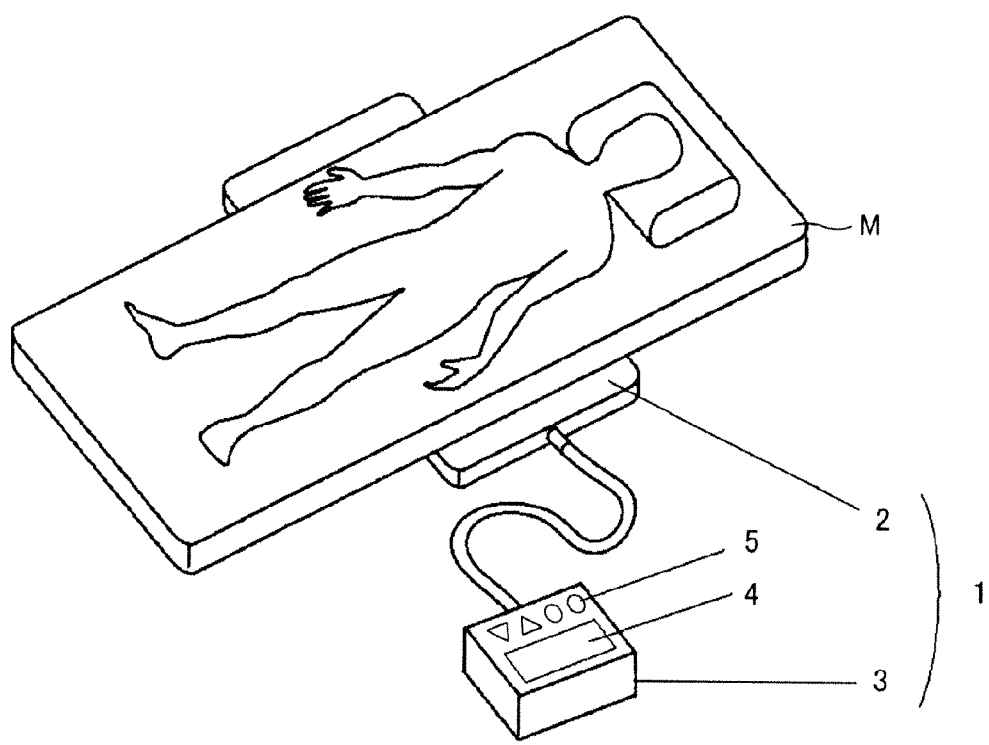
FIG. 1 shows appearance of a sleep measurement apparatus in use according to embodiments of the present invention.

FIG. 1 shows an appearance of a sleep measurement apparatus 1 in use according to embodiments of the present invention. The sleep measurement apparatus is an apparatus that measures sleeping conditions of a human subject being recumbent on a bottom bedding (e.g., a mattress for a bed or a Japanese-style mattress) M. As illustrated in FIG. 1, the sleep measurement apparatus 1 includes a sensor unit 2 and a main unit 3.

The sensor unit 2 is an element that can be used together with the bottom bedding M and that may be arranged under the bottom bedding M as illustrated in FIG. 1, for instance. The sensor unit 2 measures (detects) biological displacement (e.g., respiration, heartbeat, or body motion) of the human subject on the bottom bedding M using a microphone (e.g., a condenser microphone) as pressure change of non-compressible fluid filled in the sensor unit 2, and outputs a measurement signal that shows a measurement result of the biological displacement.

The main unit 3 is connected to the sensor unit 2 and executes a present-on-bed determination operation and a sleeping condition measurement operation based on the measurement signal output from the sensor unit 2. The main unit 3 includes a display unit 4 and an operation unit 5. The display unit 4 displays measured sleeping conditions or the like. The operation unit 5 is used for operation by the human subject and includes a power switch.

Figure 2:
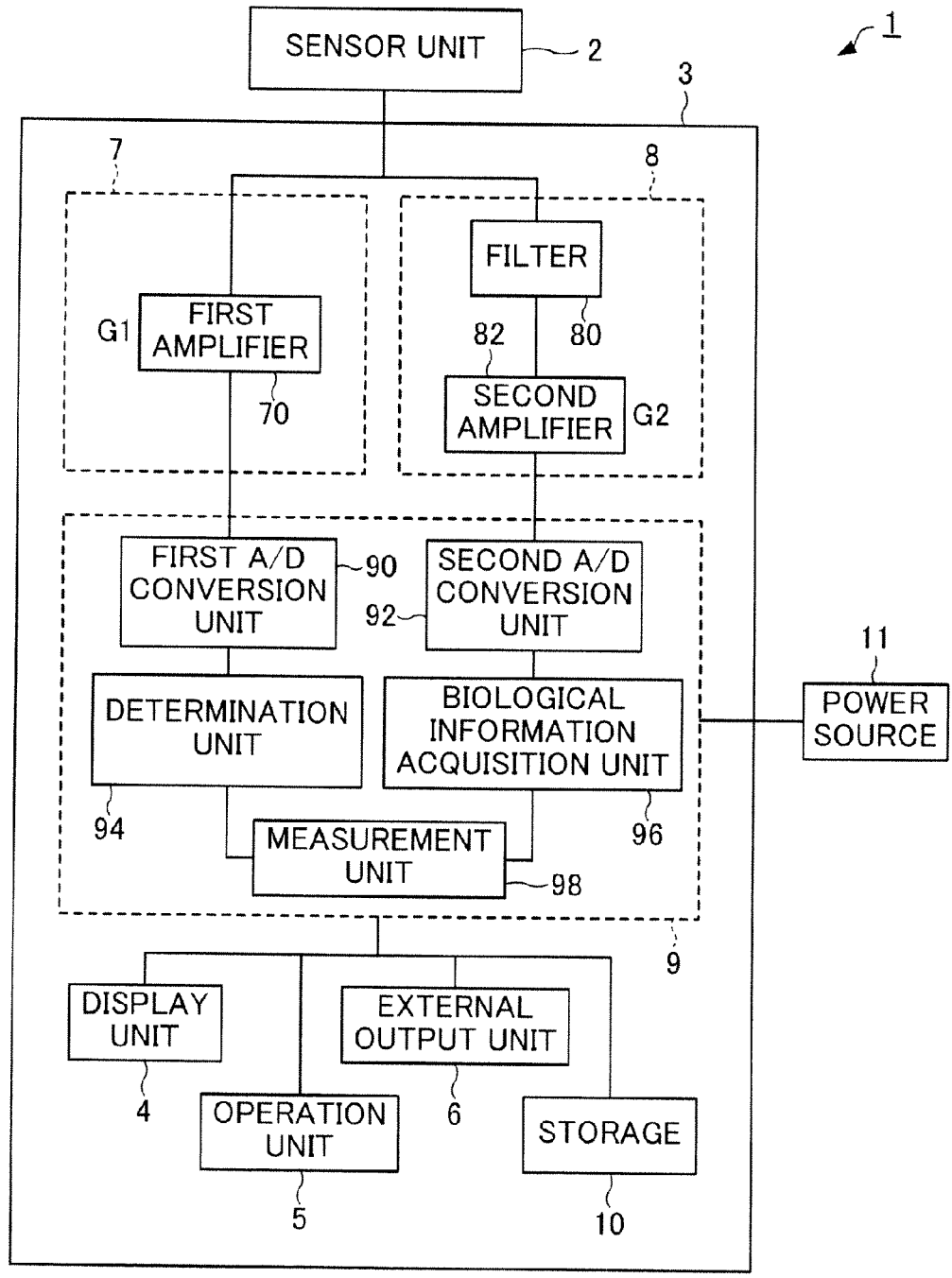
FIG. 2 is a block diagram that shows configurations of the sleep measurement apparatus.

FIG. 2 is a block diagram that shows configurations of the sleep measurement apparatus 1. The main unit 3 includes the display unit 4, the operation unit 5, an external output unit 6, a first signal processing unit 7, a second signal processing unit 8, a CPU (Central Processing Unit) 9, and storage 10. The main unit 3 is connected to a power source 11. The external output unit 6 is an interface for externally outputting results of present-on-bed determination and sleeping condition determination. For instance, the external output unit 6 may be a memory card slot or a USB interface. The storage 10 is a storage medium that is capable of storing programs and data utilized to execute the present-on-bed determination and the sleeping condition determination. For instance, the storage 10 may be a ROM, a RAM, or a combination thereof.

The first signal processing unit 7 includes a first amplifier 70. The first amplifier 70 amplifies the measurement signal output from the sensor unit 2 with a first gain G1 so as to output a first output signal to the CPU 9. The second signal processing unit 8 includes a filter 80 and a second amplifier 82. The filter 80 transmits a component corresponding to respiration of the human subject in the measurement signal output from the sensor unit 2. For instance, the filter 80 may be a low pass filter. The second amplifier amplifies the measurement signal having been transmitted through the filter 80 with a second gain G2 so as to output a second output signal to the CPU 9. The second gain G2 is smaller than the first gain G1 (i.e., G2<G1).

The CPU 9 includes a first A/D conversion unit 90, a second A/D conversion unit 92, a determination unit 94, a biological information acquisition unit 96, and a measurement unit 98. The first A/D conversion unit 90 outputs a plurality of first level values obtained by A/D conversion of the first output signal supplied from the first signal processing unit 7 (the first amplifier 70) to the determination unit 94. The determination unit 94 determines whether or not the human subject is present on the bed (i.e., on the bottom bedding M) in accordance with a standard deviation σ that indicates dispersion degree of a plurality of the first level values (further details will be given later).

The second A/D conversion unit 92 outputs a plurality of second level values obtained by A/D conversion of the second output signal supplied from the second signal processing unit 8 (the second amplifier 82) to the biological information acquisition unit 96. The biological information acquisition unit 96 calculates biological information of the human subject based on a plurality of the second level values and outputs it to the measurement unit 98. The measurement unit 98 measures sleeping conditions of the human subject based on the biological information of the human subject.

The determination unit 94, the biological information acquisition unit 96, and the measurement unit 98 are functional blocks. The CPU 9 executes computer programs stored in the storage 10 and operates in accordance with these computer programs to provide those functional blocks.

2. First Level Value

The first level value will be described in detail, which is utilized for the present-on-bed determination of the human subject. The first level value is a digital value depending on magnitude of the first output signal (analog value) that is obtained by amplifying the measurement signal with the first gain G1. In FIGS. 3 and 4, the first level values are plotted in time series. In this embodiment, since the quantization bit rate of the first A/D conversion unit 90 is 12-bit, the maximum value of the first level values is equal to 4095 ($=2^{12}-1$) and the minimum value of the first level values is equal to 0 in each figure. However, the present invention is not limited to the above-described configuration. For instance, 8-bits or 16-bits may be adapted for the quantization bit rate of the first A/D conversion unit 90.

FIG. 3 illustrates transition of the first level values when the human subject is not present on the bottom bedding M. When the human subject is not present on the bed, the magnitude of the measurement signal remains almost unchanged since the sensor unit 2 does not detect pressure changes. As a result, the first level values also remain almost unchanged and are kept near an intermediate value 2048 ($=2^{11}$). Narrow fluctuations of the first level values in FIG. 3 are due to thermal noise and so on (i.e., is not derived from the biological displacement of the human subject).

FIG. 4 illustrates transition of the first level values when the human subject is present on the bottom bedding M. When the human subject is present on the bed, the sensor unit 2 detects biological displacement of the human subject as pressure changes. Except for large body motion (rough body motion) such as a roll-over that occurs discontinuously, respiration (expansion and contraction of lungs) is dominant as biological displacement of the human subject on the bed. As a result, the transition of the first level values schematically shows a waveform corresponding to the respiration of the human subject, and one cycle of the first level values corresponds to one respiration cycle of the human subject. The respiration is a type of a cyclic component of the biological displacement.

In this embodiment, the first gain G1 is experimentally or statistically configured so that a possible maximum value and a possible minimum value of the first level values are included in a plurality of the first level values that are obtained during the one respiration cycle of the human subject. As a result, as illustrated in FIG. 4, a period $P_{max}$ in which the maximum of the first level values is maintained and a period $P_{min}$ in which the minimum of the first level values is maintained are periodically repeated. Since the first gain G1 is configured as described above, the first level values in which the human subject is present on the bottom bedding M are notably different and easily distinguishable from the first level values in which the human subject is not present on the bottom bedding M. Therefore, accuracy of the present-on-bed determination can be maintained in a case in which the sleep measurement apparatus 1 is applied to various beddings (e.g., a bed or a Japanese-style mattress) and various types of human subjects (e.g., a heavy person or a lightweight person).

As described with reference to FIGS. 3 and 4, the first level values remain almost unchanged when the human subject is not present on the bottom bedding M. On the other hand, the first level values change cyclically in line with the respiration of the human subject when he or she is present on the bottom bedding M. As a result, in general, it can be determined that the human subject is not present on the bed when the standard deviation σ that indicates dispersion degree of the first level values is small. Similarly, it can be determined that the human subject is present on the bed when the standard deviation σ is large.

However, the first level values show patterns different from FIGS. 3 and 4 when the human subject comes to be present on (or is getting into) the bottom bedding M or when some pressure caused by other than the presence of the human subject on bed is applied to the sensor unit 2.

Figure 5:
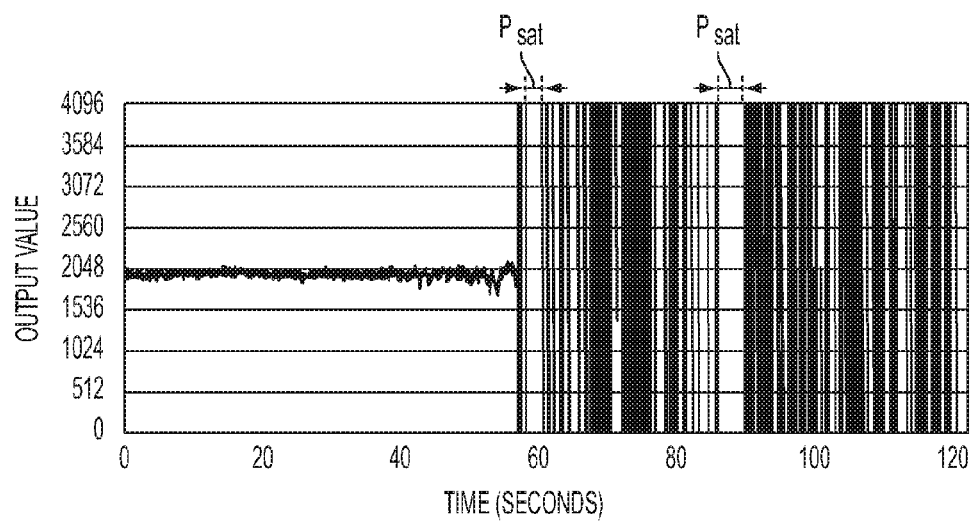
FIG. 5 illustrates an example of transition of first level values.
Figure 6:
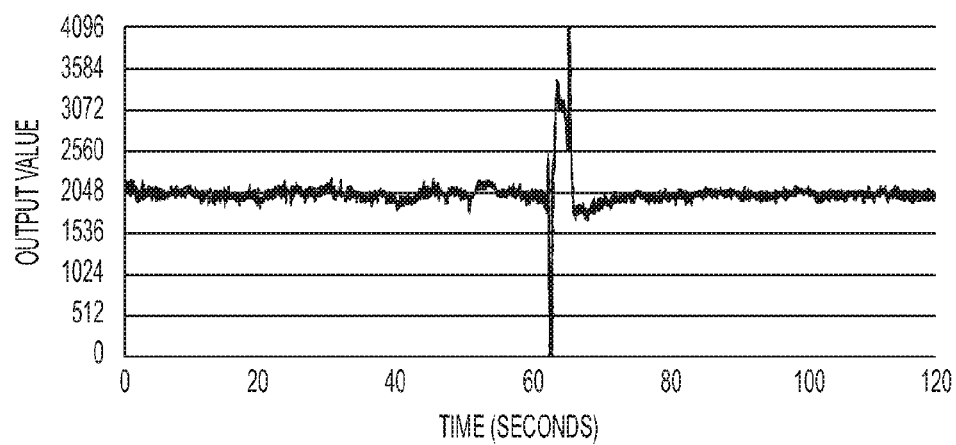
FIG. 6 illustrates an example of transition of first level values.

In FIGS. 5 and 6, the first level values are plotted in time series similar as FIGS. 3 and 4. FIG. 5 illustrates transition of the first level values when the human subject comes to be present on (or is getting on) the bottom bedding M at around the 60-second point. Compared to the case in which the human subject is already present on the bed in FIG. 4, body motion of the human subject is relatively large, so that the pressure change sensed (detected) by the sensor unit 2 becomes larger. While the pressure based on the respiration changes cyclically, pressure based on the body motion when the human subject is getting into the bed (e.g., lying motion or motion to adjust his or her position) does not change cyclically. As illustrated in FIG. 5, the first level values when the human subject is getting into the bed change noncyclically and more greatly than in the case in which the human subject is present on the bed. As a result, the first level values are notably dispersed and the standard deviation σ of the first level values is relatively large.

Since the body motion of the human subject is large and noncyclic when he or she comes to be present on the bed, there is a ease in which the maximum value or the minimum value of the first level values is maintained (i.e., the first level values are saturated) for a relatively long time such as a period $P_{sat}$ in FIG. 5. In the $P_{sat}$, although actual pressure change (measurement signal that the sensor unit 2 outputs) is large, the first level values are saturated and maintained at a constant value (the maximum or minimum value), so that the standard deviation σ becomes 0. Therefore, it can be determined that the human subject is present on the bottom bedding M not only when the standard deviation σ is large, but also when the standard deviation σ is 0. Note that there is a case in which the first level values are saturated for a relatively long time and the standard deviation σ of the first level values becomes 0, not only when the human subject is getting into the bed, but also when the body motion is large (e.g., when the human subject rolls over).

As described previously, since the measurement signal fluctuates slightly due to thermal noise or the like, the standard deviation σ of the first level values does not become 0. Accordingly, it is not determined that the human subject is present on the bed in such a case.

FIG. 6 illustrates transition of the first level values when some baggage (i.e., a non-living object) is placed on the bottom bedding M at around the 60-second point. When the baggage is placed on the bottom bedding M, the sensor unit 2 detects pressure change to output a measurement signal. As a result, the first level values are changed and dispersed at around the 60-second point, so that the standard deviation σ takes on a large value.

Since the baggage is inanimate and does not move voluntarily (i.e., does not give the biological and cyclic displacement such as respiration), it does not exert any pressure change after it is placed on the bottom bedding M and becomes stable. As a result, the first level values remain almost unchanged in a manner similar to the transition shown in FIG. 3 in which the human subject is not present on the bed and the standard deviation σ of the first level values maintains low values that are not 0.

FIG. 6 shows that temporarily high standard deviation σ of the first level values does not necessarily mean that the human subject is present on the bottom bedding M. Accordingly, it is understood that the present-on-bed determination based on the standard deviation σ of the first level values requires taking into account the standard deviations σ over a relatively long period.

3. Present-On-Bed Determination Operation

Figure 7:
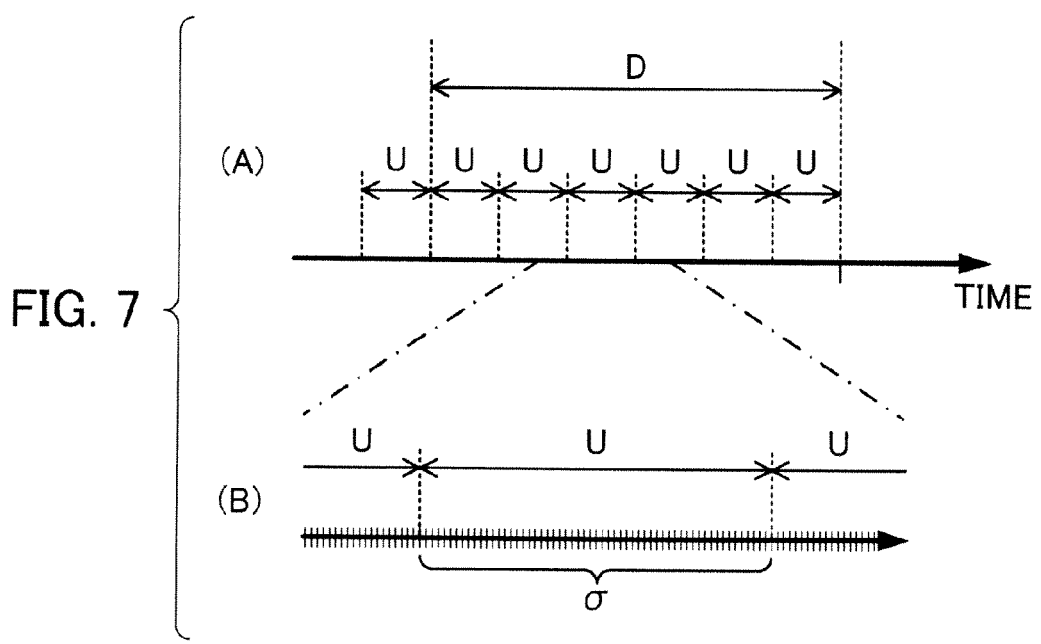
FIG. 7 shows a relationship between a determination period D that is a reference range for present-on-bed determination and a plurality of unit periods U that are included in the determination period D.

On the basis of the characteristics of the first-level-value transition as described above, the present-on-bed determination operation in this embodiment will be explained. A portion (A) of FIG. 7 shows a relationship between a determination period D that is a reference range for the present-on-bed determination and a plurality of unit periods U that are included in the determination period D. A portion (B) of FIG. 7 shows with magnification some of the unit periods U which are included in the portion (A) of FIG. 7. Each time length of the unit periods U is predetermined (e.g., five seconds in this embodiment). Specifically, the time length of the unit period U is experimentally or statistically configured so that the time period exceeds a time length required for one respiration cycle of the human subject.

In the portion (B) of the FIG. 7, a plurality of vertical lines included in each unit period U means that a plurality of the first level values are obtained during each unit period U. The standard deviations is calculated based on the first level values obtained in the unit period U. That is, the standard deviation σ of the first level values is calculated per one unit period U.

As explained above with reference to FIG. 6, temporal fluctuation of the first level values (i.e., temporal increase of the standard deviation σ) does not necessarily mean that that the human subject is present on the bottom bedding M. Accordingly, as shown in the portion (A) of FIG. 7, the present-on-bed determination is executed using a plurality of the standard deviations σ calculated in each of the unit periods U which are included in the determination period D.

Figure 8:
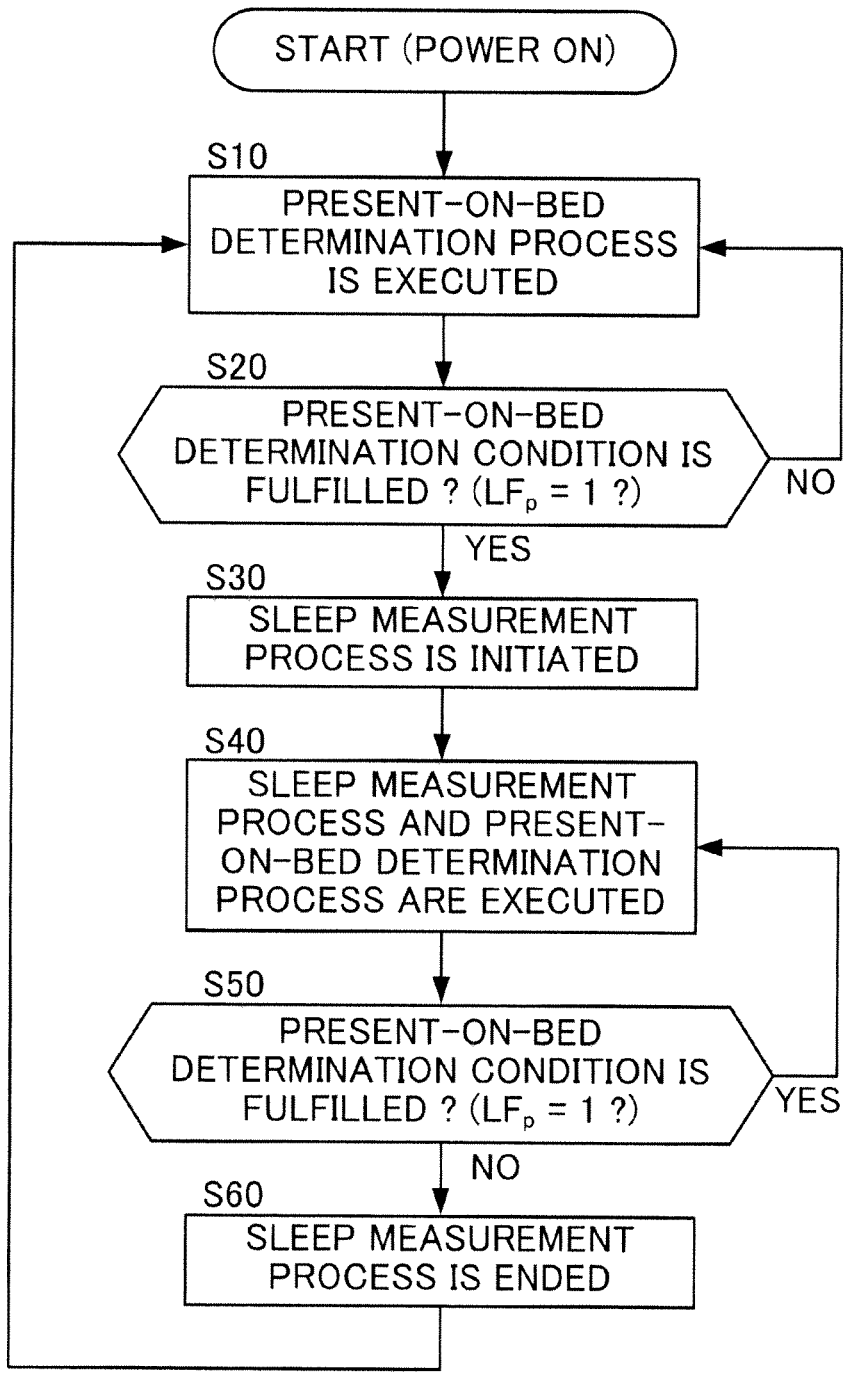
FIG. 8 is a flowchart that illustrates an overall operation executed in the sleep measurement apparatus.
Figure 9:
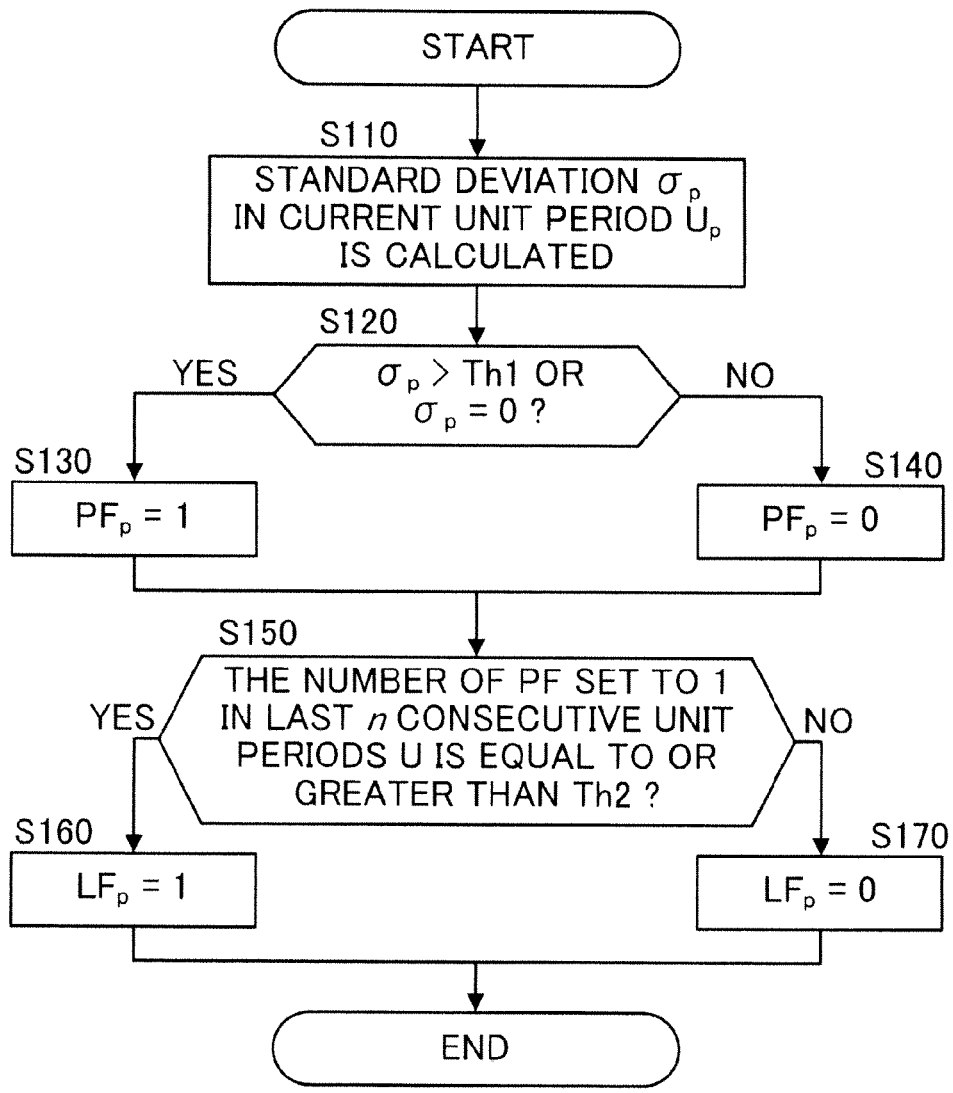
FIG. 9 is a flowchart that illustrates a present-on-bed determination operation according to a first embodiment in which the human subject is not present on the bed.
Figure 10:
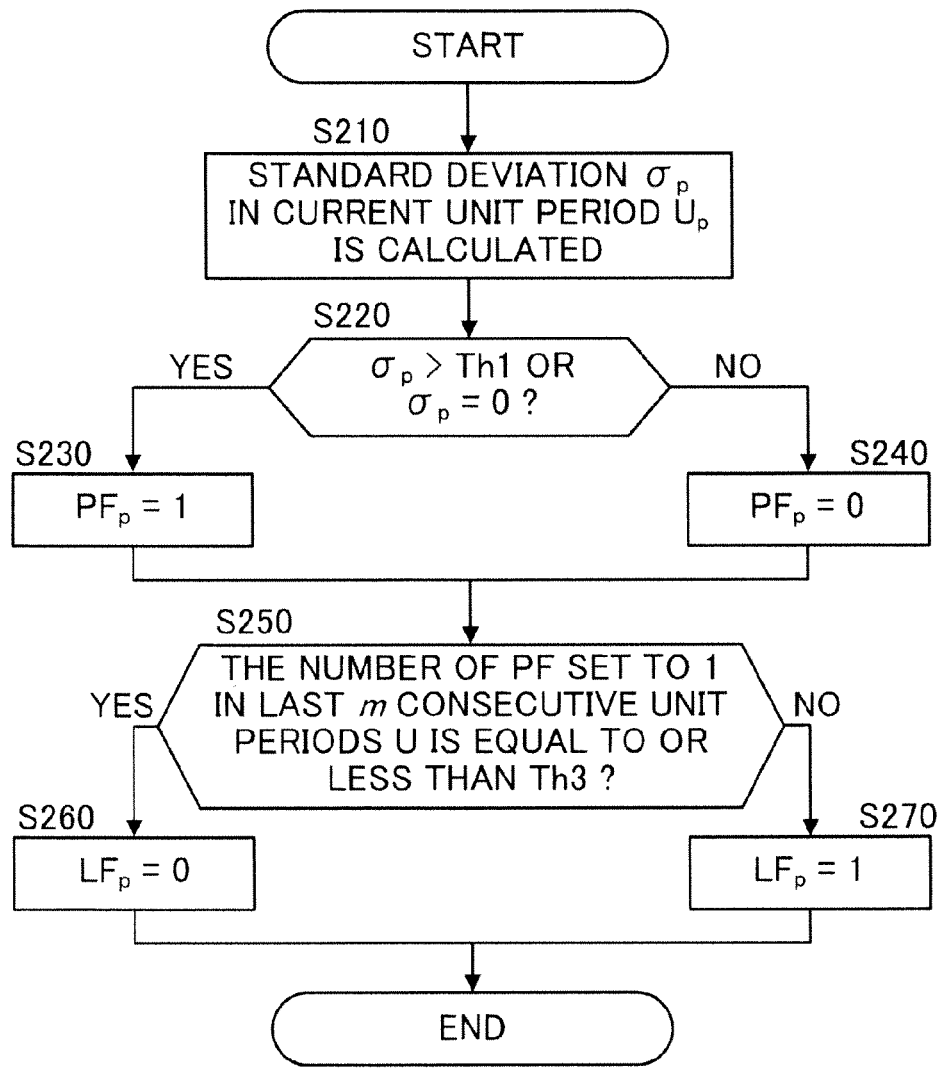
FIG. 10 is a flowchart that illustrates a present-on-bed determination operation according to a first embodiment in which the human subject is present on the bed.

The present-on-bed determination operation will be described in detail with reference to flowcharts in FIGS. 8 to 10, and FIGS. 11 and 12. FIG. 8 is a flowchart that illustrates an overall operation executed in the sleep measurement apparatus 1. FIG. 9 is a flowchart that illustrates a present-on-bed determination operation in which the human subject is not present on the bed. FIG. 10 is a flowchart that illustrates a present-on-bed determination operation in which the human subject is present on the bed.

If the power switch of the operation unit 5 is manipulated to turn on the sleep measurement apparatus 1, a timer (not shown) in the CPU 9 begins to count elapsed time from when turning on the sleep measurement apparatus 1 and the CPU 9 (determination unit 94) executes a present-on-bed determination process (S10). If it is determined that the human subject is present on the bottom bedding M (i.e., present-on-bed determination condition is fulfilled) in the present-on-bed determination process (S20: YES), the CPU 9 (the second A/D conversion unit 92, the biological information acquisition unit 96, and the measurement unit 98) begins to execute a sleep measurement process (S30). On the other hand, if it is determined that the human subject is not present on the bottom bedding M (i.e., the present-on-bed determination condition is not fulfilled) (S20: NO), the CPU 9 repeats the present-on-bed determination process (S 10).

The present-on-bed determination process in the step S10 will be described in detail with reference to FIG. 9. Hereinafter, in a case in which a plurality of the unit periods U are necessary to be distinguished from each other, a subscript indicating a time point when the unit period U is finished (i.e., elapsed time from power activation) is added to the reference mark "U" (for instance, if the unit period U is finished at time t=5 seconds, it will be stated as $U_5$). The same is applied to other reference marks (for instance, if the determination period D is finished at time t=30 seconds, it will be stated as $D_{30}$). Time t=p represents present (current) time.

When the present-on-bed determination process begins, the determination unit 94 calculates a standard deviation $\sigma_p$ of a plurality of first level values included in the current unit period $U_p$ (S110). Specifically, the first A/D conversion unit 90 performs A/D conversion with a first output signal at a predetermined frequency (e.g., 16 Hz) in the current unit period $U_p$ to obtain plural (e.g., 80) first level values, which are supplied to the determination unit 94. The determination unit 94 calculates the standard deviation $\sigma_p$ of the plurality of the first level values obtained during the current unit period $U_p$ and writes it in a determination table T in the storage 10.

Subsequently, the determination unit 94 determines whether or not the calculated standard deviation $\sigma_p$ exceeds a first threshold Th1 (e.g., 500) or is equal to 0 (S120). Hereinafter, the above determination condition may be called "preliminary condition" and the above determination itself may be called "preliminary determination". As described above, the preliminary determination is intended to determine whether or not the human subject is present on the bottom bedding M, and a plurality of preliminary determination results will be utilized in the present-on-bed determination.

If the preliminary condition is fulfilled, that is, if the standard deviation $\sigma_p$ exceeds the first threshold Th1 or is equal to 0 (S120: YES), the determination unit 94 sets a preliminary determination flag $PF_p$ corresponding to the unit period $U_p$ in the determination table T to 1 (S 130). On the other hand, if the preliminary condition is not fulfilled, that is, if the standard deviation $\sigma_p$ does not exceed the first threshold Th1 and is not equal to 0 (S 120: NO), the determination unit 94 sets the preliminary determination flag $PF_p$ to 0 (S140).

After setting the preliminary determination flag $PF_p$, the determination unit 94 determines whether or not the human subject is present on the bottom bedding M in the current unit period $U_p$ (S150). Specifically, if the number of cases in which the preliminary condition is fulfilled (i.e., the number of the preliminary determination flags PF which are set to 1) in the determination period D (i.e., the last n (e.g., 6) consecutive unit periods U including the current unit period $U_p$) is equal to or greater than a second threshold Th2 (e.g., 5), the determination unit 94 determines that the human subject is present on the bed in the current unit period $U_p$, and otherwise it determines that the human subject is not present on the bed.

If the number of the last consecutive unit period U is less than n, processes after the step S150 may be skipped, or the process of the step 150 may be executed with assuming the values of the preliminary determination flags PF regarding lacking unit periods U as 0.

If it is determined that the human subject is present on the bottom bedding M (S150: YES), the determination unit 94 sets a present-on-bed determination flag $LF_p$ corresponding to the current unit period $U_p$ to 1 (S 160). In contrast, if it is determined that the human subject is not present on the bottom bedding M (S 150: NO), the determination unit 94 sets the present-on-bed determination flag $LF_p$ to 0 (S 160). After setting the present-on-bed determination flag LF, a single present-on-bed determination process (S10) ends.

As described above, if the present-on-bed determination condition in the step S150 is fulfilled (i.e., the present-on-bed determination flag $LF_p$ is set to 1), a sleep measurement process is initiated (S30). If the sleep measurement process starts, while the measurement unit 98 executes the sleep measurement process, the determination unit 94 executes a present-on-bed determination process (S40). As long as the present-on-bed determination condition is fulfilled (S50: YES), the CPU 9 continues to execute the sleep measurement process and the present-on-bed determination process. On the other hand, it is determined that the present-on-bed determination condition is not fulfilled (S50: NO), the CPU 9 (measurement unit 98) terminates the sleep measurement process and returns to the step S10 (i.e., waits for a human subject to comes to be present on the bed).

The present-on-bed determination process in the step S40 will be described in detail with reference to FIG. 10. Although both of the processes in the steps (FIG. 9 and FIG. 10) are nearly identical, conditions of present-on-bed determination processes (conditions in steps S150 and S250) are different from each other. A process for calculating a standard deviation $\sigma_p$ in current unit period $U_p$ (S210) to a process for setting a preliminary determination flag $PF_p$ (S230 or S240) are identical to the processes in the step S10 (the steps S110 to S140), so explanation will be omitted. The first threshold Th1 of the preliminary condition in the step S120 may be different from that in the step S220.

After setting the preliminary determination flag $PF_p$ (S230, S240), the determination unit 94 determines whether or not the human subject is present on the bottom bedding M in the current unit period $U_p$ (S250). Specifically, if the number of cases in which the preliminary condition is fulfilled (i.e., the number of the preliminary determination flags PF which are set to 1) in the determination period D (i.e., the last m (e.g., 6) consecutive unit periods U including the current unit period $U_p$) is equal to or less than a third threshold Th3 (e.g., 1), the determination unit 94 determines that the human subject is not present on the bed in the current unit period $U_p$, otherwise it determines that the human subject is present on the bed. The number of the unit periods U included in one determination period D in the step S150 may be different from that in the step S250.

If it is determined that the human subject is not present on the bottom bedding M (S250: YES), the determination unit 94 sets a present-on-bed determination flag $LF_p$ corresponding to the current unit period $U_p$ to 0 (S260). While if it is determined that the human subject is present on the bottom bedding M (S250: NO), the determination unit 94 sets the present-on-bed determination flag $LF_p$ to 1 (S270). After setting the present-on-bed determination flag LF, a single present-on-bed determination process (S40) ends. Operations after that (i.e., the steps S50 and S60) are previously described.

An example of determination results (i.e., the determination table T) according to the present-on-bed determination process described above will be described with reference to FIGS. 11 and 12. FIG. 11 illustrates determination results in which the human subject comes to be present on the bottom bedding M at around time t=60 seconds. The preliminary determination flags PF until time t=55 seconds are set to 0 since the human subject is not present on the bed and the standard deviation σ of the first level values is small.

On or after time t=60 seconds, the preliminary determination flags PF are set to 1 since the human subject is present on the bed and the standard deviation 6 of the first level values is large. However, until time t=75 seconds, the present-on-bed determination flags LF are set to 0 since the number of the preliminary determination flags PF which are set to 1 in the respective determination periods D is less than 5. On the other hand, on or after time t=80 seconds, the present-on-bed determination flags LF are set to 1 since the number of the preliminary determination flags PF which are set to 1 in the respective determination periods D is equal to or greater than 5.

FIG. 12 illustrates determination results in which the human subject comes not to be present on (i.e., leaves) the bottom bedding M at around time t=270 seconds. The preliminary determination flags PF until time t=270 seconds are set to 1 since the human subject is present on bed and the standard deviation σ of the first level values is large or is equal to 0.

On or after time t=275 seconds, the preliminary determination flags PF are set to 0 since the human subject is not present on the bed and the standard deviation σ of the first level values is small. However, until time t=290 seconds, the present-on-bed determination flags LF are set to 1 since the number of the preliminary determination flags PF which are set to 1 in the respective determination periods D is greater than 1. On the other hand, on or after time t=295 seconds, the present-on-bed determination flags LF are set to 0 since the number of the preliminary determination flags PF which are set to 1 in the respective determination periods D is equal to or less than 1.

In around time t=300 seconds, the standard deviation σ temporarily increases depending on noise. However, the present-on-bed determination process with taking into account the standard deviations σ in a plurality of the unit periods U included in one of the determination periods D does not provide an erroneous determination that the human subject is present on the bed.

According to the above-described configurations of this embodiment, in a case in which the human subject is not present on the bed, it is determined that the human subject comes to be present on (or is getting into) the bed if the preliminary conditions are fulfilled with a high frequency. In contrast, in a case in which the human subject is present on the bed, it is determined that the human subject comes not to be present on (or leaves) the bed if the preliminary conditions are fulfilled with a low frequency. As a result, an erroneous determination that the human subject is present on the bed based on the temporary increase of the standard deviation σ depending on noise such as described in FIG. 6 can be prevented. Similarly, an erroneous determination that the human subject is not present on the bed based on the temporary decrease of the standard deviation σ in which the human subject is present on the bed can be prevented.

The human subject tends to forget to give instructions to initiate and to terminate the sleep measurement process since sleep is an unremarkable behavior for him or her. According to the configurations of this embodiment, it is automatically determined whether or not the human subject is present on the bed, so that the sleep measurement process is initiated or terminated, which provides the human subject with greater convenience.

Second Embodiment

A second embodiment of the present invention will be described. Note that elements whose actions and functions are equivalent to those of the first embodiment in respective modes illustrated below are identified by the same reference numerals as in the above description, and detailed description thereof is appropriately omitted.

In the first embodiment, the change of the first level values based on the biological displacement is obtained as the standard deviation σ the first level values, so that the present-on-bed determination of the human subject is executed. In the second embodiment, the change of the first level values based on the biological displacement is obtained as a result of frequency analysis on the first level values, so that present-on-bed determination of the human subject is executed.

1. Configurations of Sleep Measurement Apparatus

A sleep measurement apparatus 1 according to the second embodiment is configured in a similar way to that of the first embodiment (FIG. 2, etc.). However, in the second embodiment, the determination unit 94 of the CPU 9 executes frequency analysis on a plurality of the first level values to obtain a noise component (i.e., first component) that is not derived from the biological displacement of the human subject and a biosignal component (i.e., second component) that is derived from the biological displacement, and determines whether or not the human subject is present on the bed in accordance with a ratio between the noise component and the biosignal component. Further details will be given below.

2. First Level Value

As explained in the first embodiment, the first level value is a digital value depending on magnitude of the first output signal (analog value) that is obtained by amplifying the measurement signal with the first gain G1. FIG. 13 exemplifies transition of the first level values when the human subject is present on the bottom bedding M. In FIG. 13, similar to FIG. 3, the first level values are plotted in time series.

As explained in the first embodiment, the first level values change in accordance with the biological displacement of the human subject. Since respiration and heartbeat that are the biological displacement of the human subject occur cyclically, a sequence of the first level values includes frequency components corresponding to the biological displacement (respiration and heartbeat). Therefore, frequency analysis on a time waveform of the first level values using a method such as a Fourier analysis provides a frequency component (frequency spectrum) that is derived from the biological displacement.

FIG. 14 illustrates a frequency waveform obtained by frequency analysis on the time waveform shown in FIG. 13. The frequency analysis is executed by the determination unit 94. In the waveform shown in FIG. 14, components which are mainly derived from the biological displacements of the human subject are distributed in a range from approximately 0.15 Hz to approximately 2.0 Hz. There are two amplitude value peaks of components derived from the biological displacement of the human subject at around 0.3 Hz and around 0.6 Hz. Any analysis method to convert a time waveform to a frequency spectrum may be adopted for frequency analysis executed by the determination unit 94. For instance, fast Fourier transform (FFT) and other methods derived therefrom may be adopted.

Figure 15:
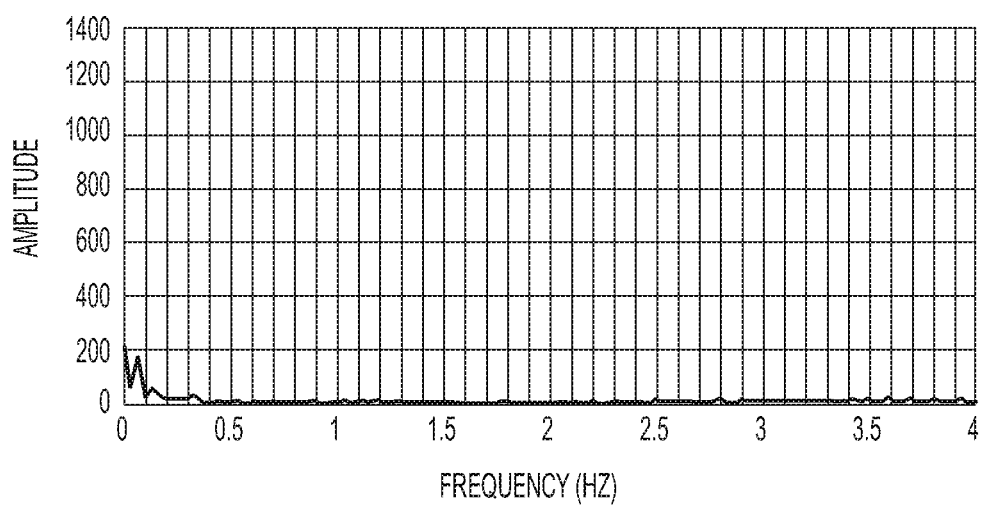
FIG. 15 illustrates another example of a frequency waveform obtained by frequency analysis on a time waveform of first level values.

FIG. 15 illustrates a frequency waveform (spectrum) that is obtained by frequency analysis on a time waveform of the first level values in a case in which the human subject is not present on the bottom bedding M. The frequency analysis is executed by the determination unit 94. In contrast with the waveform shown in FIG. 14, in the waveform shown in FIG. 15, amplitude values of components derived from the biological displacement of the human subject (i.e., components ranging from approximately 0.15 Hz to approximately 2.0 Hz) are close to 0, and there is no amplitude value peak. In FIG. 15, amplitude values of low-frequency (less than approximately 0.15 Hz) components (low-frequency noise components) are greater than those in other frequency ranges. A possible but non-limiting cause for such low-frequency noise is low-frequency oscillation of a building in which the sleep measurement apparatus 1 is located. An example of the low-frequency oscillation is oscillation generated by, for example, building-induced wind. Further, although not shown in FIG. 15, high-frequency noise components that are not derived from the biological displacement in a high frequency range (greater than approximately 2.0 Hz) can be observed in the frequency waveform of the first level values when there is building construction or car traffic around the building in which the sleep measurement apparatus 1 is located. A cause for high-frequency noise is not limited to the possible cause described above (i.e., construction or car traffic).

As explained with reference to FIGS. 14 and 15, when the human subject is present on the bottom bedding M, the result of the frequency analysis on the first level values includes the components derived from the biological displacement. In contrast, when the human subject is not present on the bottom bedding M, the result of the frequency analysis on the first level values does not include the components derived from the biological displacement. Therefore, whether or not the human subject is present on the bottom bedding M can be determined based on whether or not the components derived from the biological displacement are included in the result of the frequency analysis on the first level values.

Figure 16:
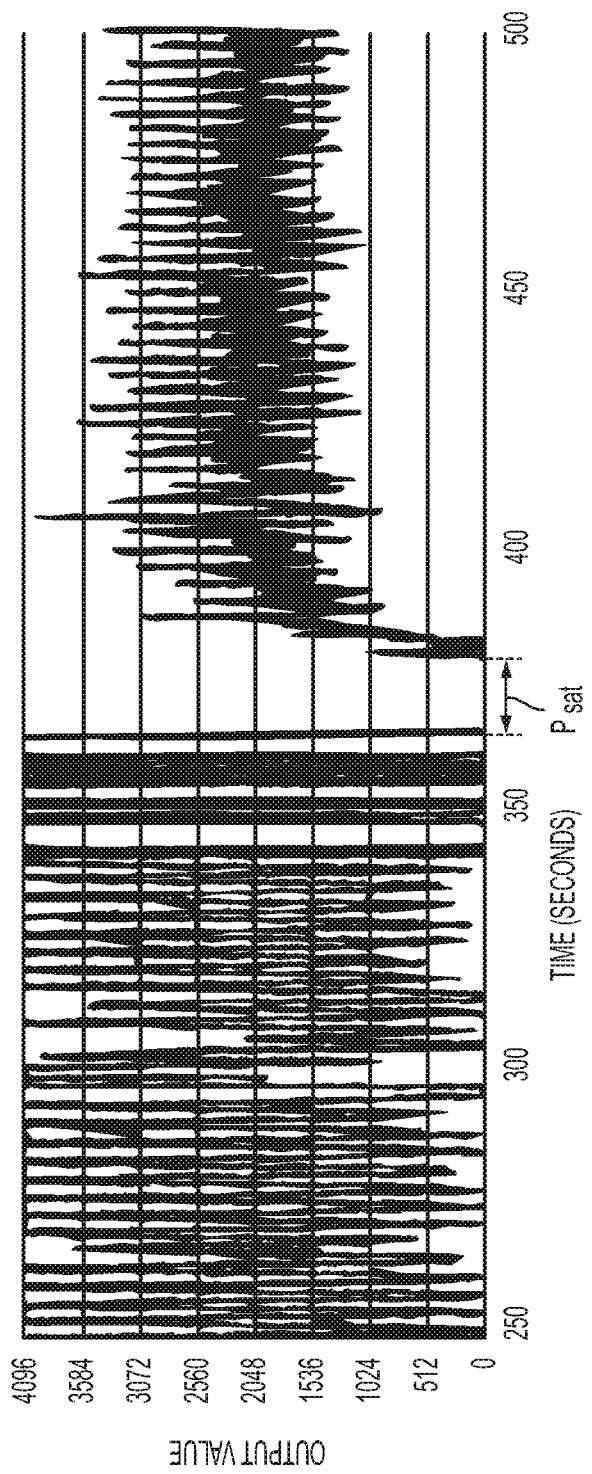
FIG. 16 illustrates an example of transition of first level values.

Further characteristics of the first level values will be explained with reference to FIGS. 16 and 17. FIG. 16 exemplifies transition in time series of the first level values over a longer time span than that of FIG. 13. In FIG. 16, the human subject on the bottom bedding M rolls over from around the 350-second point to around the 380-second point. As a result, the first level values change greatly and noncyclically, and then the first level values are saturated during a period $P_{sat}$. After the roll-over (i.e., after around the 380-second point), output values (fluctuation range) of the first level values are decreased compared to those before the roll-over (i.e., before around the 350-second point). The above-described decrease of the output values (fluctuation range) is derived from decrease of pressure change of the sensor unit 2 based on the biological displacement (e.g., expansion and contraction of lungs). The decrease of pressure change is caused by posture change associated with the roll-over of the human subject on the bottom bedding M (e.g., change from a face-down posture to a sideways posture).

FIG. 17 illustrates a frequency waveform (spectrum) that is obtained by frequency analysis on a partial time waveform after the roll-over included in the time waveform shown in FIG. 16. The frequency analysis is executed by the determination unit 94. In the waveform shown in the FIG. 17, similar to FIG. 14, components which are mainly derived from the biological displacement of the human subject are distributed in a range less than approximately 2.0 Hz, and there are two amplitude value peaks of components derived from the biological displacement of the human subject at around 0.3 Hz and around 0.6 Hz. However, as described previously, the output values (fluctuation range) are decreased after the roll-over. As a result, amplitude values of the components derived from the biological displacement are decreased compared to FIG. 14.

According to the above comparison between FIGS. 14 and 17, it will be understood that, even if the human subject is present on the bottom bedding M, magnitude of the components derived from the biological displacement varies depending on, for example, a posture of the human subject. As a result, if whether or not the human subject is present on the bottom bedding M is determined based on determination criteria such as "a component value derived from biological displacement is greater than a predetermined threshold", it is likely to be determined that the human subject is not on the bed although the human subject is actually present on the bottom bedding M, in a case in which the output values (fluctuation range) of the first level values are decreased as after the roll-over in FIG. 16.

In this embodiment, frequency analysis is executed on first level values output during a predetermined analysis period A to obtain a noise component (i.e., first component) that is not derived from biological displacement and a biosignal component (i.e., second component) that is derived from biological displacement, so that present-on-bed determination is executed in accordance with a ratio (spectral ratio) between the noise component and the biosignal component. The analysis period A contains a time period corresponding to several respiration cycles of the human subject. For instance, the analysis period A is a period with 30 seconds.

3. Present-On-Bed Determination Operation

Figure 19:
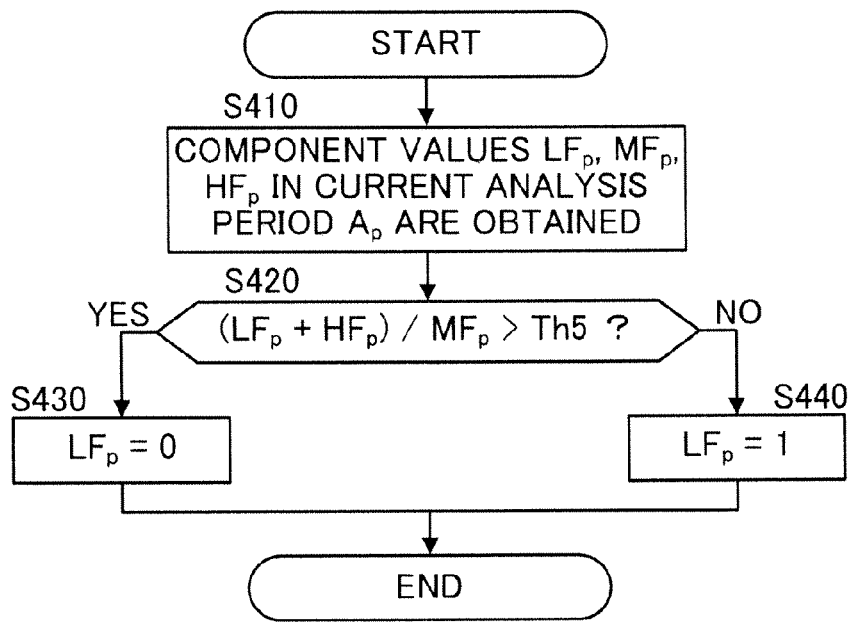
FIG. 19 is a flowchart that illustrates a present-on-bed determination operation according to a second embodiment in which the human subject is present on the bed.

The present-on-bed determination operation in the second embodiment will be explained with reference to FIGS. 8, 18, and 19. An overall operation executed in the sleep measurement apparatus 1 is similar to that of the first embodiment explained with reference to FIG. 8. FIG. 18 is a flowchart that illustrates a present-on-bed determination operation in a condition in which the human subject is not present on the bed. FIG. 19 is a flowchart that illustrates a present-on-bed determination operation in a condition in which the human subject is present on the bed.

Similar to the first embodiment, when the sleep apparatus 1 is powered on, the CPU 9 (determination unit 94) executes a present-on-bed determination process (S10).

The present-on-bed determination process (S310 to S340) in the step S10 will be described in detail with reference to FIG. 18. When the present-on bed determination process begins, the determination unit 94 executes frequency analysis on the first level values to obtain a noise component (first component) and a biosignal component (second component). Specifically, the first A/D conversion unit 90 performs A/D conversion with a first output signal at a predetermined frequency (e.g., 16 Hz) in the current analysis period $A_p$ that includes the current time point to obtain plural first level values, and outputs the plural first level values to the determination unit 94. The determination unit 94 executes frequency analysis on the first level values supplied from the first A/D conversion unit 90 to obtain a component value $LC_p$ of a low-frequency range (e.g., less than 0.15 Hz), a component value $MC_p$ of a mid-frequency range (e.g., greater than 0.15 Hz and less than 2 Hz), and a component value $HC_p$ of a high-frequency range (e.g., greater than 2 Hz) (S310). Each of the component values may be calculated as an integrated value of amplitude values in each frequency range or be calculated as an amplitude value at a predetermined frequency. A sum of the component value $LC_p$ of the low-frequency range and the component value $HC_p$ of the high-frequency range (i.e., $LC_p+HC_p$) corresponds to the noise component. The component value $MC_p$ of the mid-frequency range corresponds to the biosignal component. The above frequencies (0.15 Hz, 2 Hz) marking the boundaries between components are non-limiting examples, so that any frequency can be adopted.

Subsequently, the determination unit 94 calculates a ratio (($LC_p$+$HC_p$)/$MC_p$) between the obtained noise component ($LC_p$+$HC_p$) and the obtained biosignal component ($MC_p$), and determines whether or not the ratio is less than a fourth threshold Th4 (e.g., one) (S320). Since the numerator of the ratio is the noise component and the denominator of the ratio is the biosignal component, the ratio becomes smaller when the biosignal component becomes larger relative to the noise component. The determination unit 94 determines that the human subject is present on the bed if the ratio is less than the fourth threshold Th4 (S320: YES), and sets a present-on-bed determination flag $LF_p$ to 1 (S330). On the other hand, the determination unit 94 determines that the human subject is not on the bed if the ratio is equal to or greater than the fourth threshold Th4 (S320: NO), and sets the present-on-bed determination flag $LF_p$ to 0 (S340). After setting the present-on-bed determination flag LF, a single present-on-bed determination process (S10) ends.

As shown in FIG. 8, if the present-on-bed determination condition is fulfilled (i.e., the present-on-bed determination flag $LF_p$ is set to 1) (S20: YES), the CPU 9 initiates a sleep measurement process (S30). On the other hand, if the present-on-bed determination condition is not fulfilled (i.e., the present-on-bed determination flag $LF_p$ is set to 0) (S20: NO), the CPU 9 repeats the present-on-bed determination process (S10).

If the sleep measurement process starts, while the measurement unit 98 executes the sleep measurement process, the determination unit 94 executes a present-on-bed determination process (S40). The present-on-bed determination process (S410 to S440) in the step 40 will be described in detail with reference to FIG. 19. Although both of the present-on-bed determination processes in FIGS. 18 and 19 are nearly identical, conditions of present-on-bed determination processes (conditions in steps S320 and S420) are different from each other. Since an operation of the step S410 (obtaining each component value) is similar to that of the step S310, further explanation will be omitted.

The determination unit 94 calculates a ratio (($LC_p$+$HC_p$)/$MC_p$) in a similar fashion to the step S320, and determines whether or not the ratio exceeds a fifth threshold Th5 (e.g., one) (S420). The fifth threshold Th5 may be identical to or different from the fourth threshold Th4. If the ratio exceeds the fifth threshold Th5, the determination unit 94 determines that the human subject is not present on the bottom bedding M (S420: YES), and sets the present-on-bed determination flag $LF_p$ to 0 (S430). On the other hand, if the ratio is equal to or less than the fifth threshold Th5, the determination unit 94 determines that the human subject is present on the bed (S420: NO), and sets the present-on-bed determination flag $LF_p$ to 1 (S440). After setting the present-on-bed determination flag LF, a single present-on-bed determination process (S40) ends.

As shown in FIG. 8, if the present-on-bed determination condition is fulfilled (i.e., the present-on-bed determination flag $LF_p$ is set to 1) (S50: YES), the CPU 9 continues to execute the sleep measurement process and the present-on-bed determination process (S40). On the other hand, if the present-on-bed determination condition is not fulfilled (i.e., the present-on-bed determination flag $LF_p$ is set to 0) (S50: NO), the CPU 9 (measurement unit 98) terminates the sleep measurement process and returns to the step S10 (i.e., waits for a human subject to come to be present on the bed).

According to the above-described embodiment, in the case in which the human subject is not present on the bed, it is determined that the human subject is (has come to be) present on the bed if the ratio is less than the threshold (fourth threshold Th4). In contrast, in the case in which the human subject is present on the bed, it is determined that the human subject is not present on (leaves) the bed if the ratio is greater than the threshold (fifth threshold Th5). As described above, the ratio is utilized to execute the determination. As a result, it is determined that the human subject is present on the bed when the biosignal component is relatively greater than the noise component (i.e., the ratio is small), even if absolute values of the biosignal component change. Therefore, as explained previously with comparing FIGS. 14 and 17, an erroneous deteimination that the human subject is not present on (leaves) the bed based on fluctuations (decrease) of the first level values caused by posture change can be prevented. An erroneous determination that the human subject is (has come to be) present on the bed based on continuing noise components not derived from the biological displacement can also be prevented. Furthermore, similar to the first embodiment, it is automatically determined whether or not the human subject is present on the bed, which provides the human subject with greater convenience.

Third Embodiment

The above-described present-on-bed determination operations in the first embodiment and the second embodiment can be combined. Such combined present-on-determination operations provide more accurate present-on-bed determination. In a third embodiment, an example of combined present-on-bed determination operations will be explained.

1. Configurations of Sleep Measurement Apparatus

Figure 20:
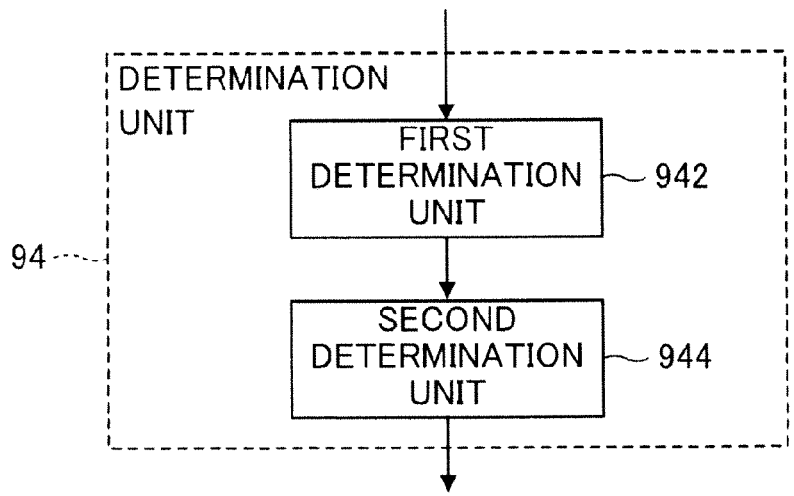
FIG. 20 illustrates a detailed configuration of a determination unit in a sleep measurement apparatus according to a third embodiment.

A sleep measurement apparatus 1 according to the third embodiment is configured in a similar way to that of the first embodiment (in particular, FIG. 2). FIG. 20 illustrates a detailed configuration of the determination unit 94. The determination unit 94 according to the third embodiment includes a first determination unit 942 that executes the determination executed by the determination unit 94 in the first embodiment and a second determination unit 944 that executes the determination executed by the determination 94 in the second embodiment. The above elements included in the determination unit 94 are functional blocks. The CPU 9 executes computer programs stored in the storage 10 and operates in accordance with these computer programs to provide those functional blocks. A single functional block may possess the functions of the first determination unit 942 and the second determination unit 944.

2. Present-On-Bed Determination Operation

Figure 21:
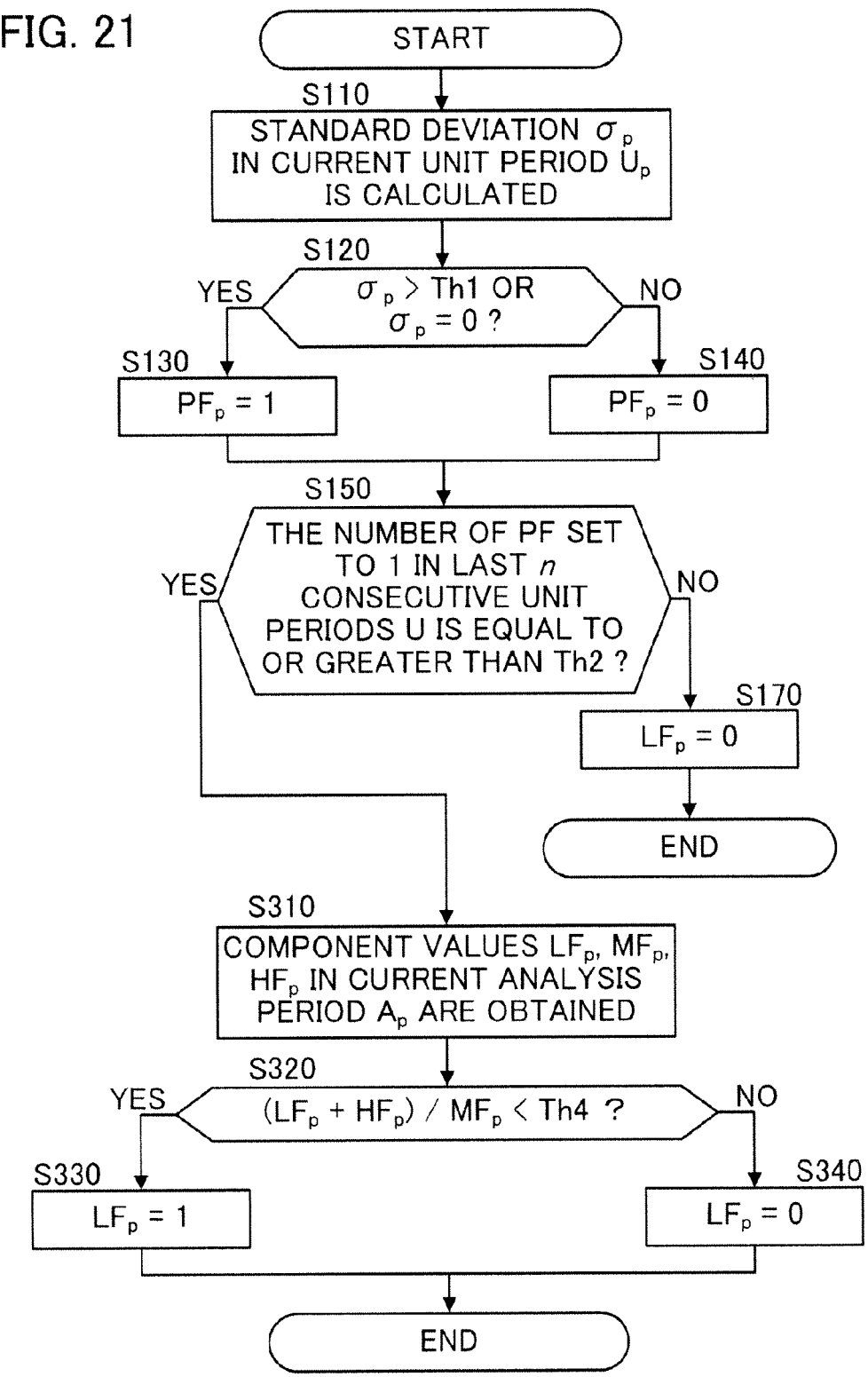
FIG. 21 is a flowchart that illustrates a present-on-bed determination operation according to a third embodiment in which the human subject is not present on the bed.
Figure 22:
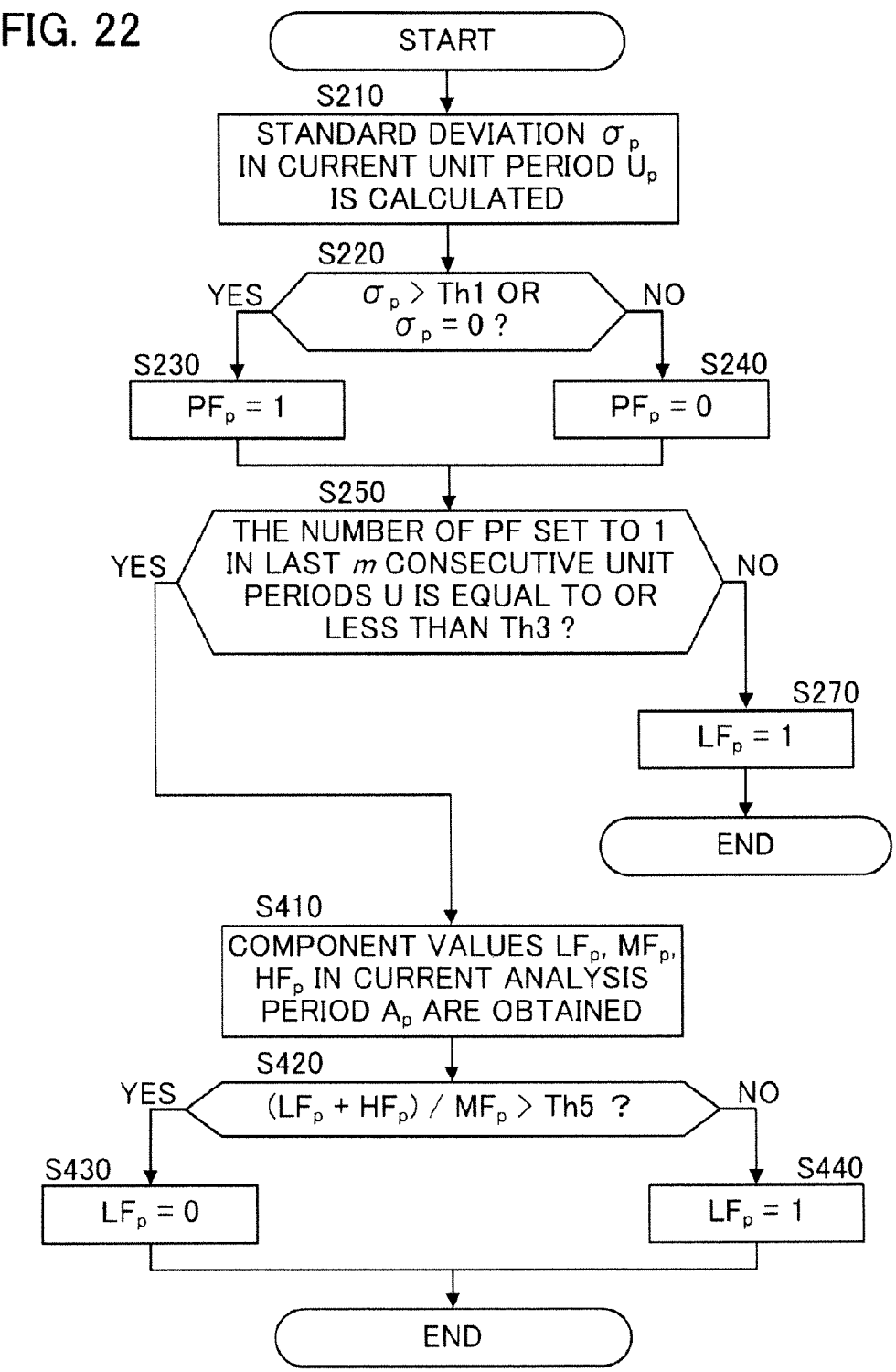
FIG. 22 is a flowchart that illustrates a present-on-bed determination operation according to a third embodiment in which the human subject is present on the bed.

The present-on-bed determination operation in the third embodiment will be explained with reference to FIGS. 8, 21, and 22. An overall operation executed in the sleep measurement apparatus 1 is similar to that of the first embodiment explained with reference to FIG. 8. FIG. 21 is a flowchart that illustrates a present-on-bed determination operation in a condition in which the human subject is not present on the bed, which schematically is a combination of the flowcharts of FIGS. 9 and 18. FIG. 22 is a flowchart that illustrates a present-on-bed determination operation in a condition in which the human subject is present on the bed, which schematically is a combination of the flowcharts of FIGS. 10 and 19.

A present-on-bed determination process in the step S10 (S110 to S340) will be explained with reference to FIG. 21. The first determination unit 942 executes a present-on-bed determination process (S110 to S170) based on a standard deviation $\sigma_p$, which is similar to the first embodiment. If it is determined that the human subject is not present on the bottom bedding M (S 150: NO), the first determination unit 942 sets a present-on-bed determination flag $LF_p$ to 0 (S 170) and a single present-on-bed determination process (S 10) ends. On the other hand, if it is determined that the human subject is present on the bottom bedding M (S 150: YES), the first determination unit 942 generates a signal (information) showing that the human subject is present on the bed to supply the second determination unit 944 therewith.

If the first determination unit 942 has determined that the human subject is present on the bed, the second determination unit 944 executes a present-on-bed determination process (S310 to S340) based on frequency analysis, which is similar to the second embodiment. If it is determined that the human subject is present on the bottom bedding M (S320: YES), the second determination unit 944 sets the present-on-bed determination flag $LF_p$ to 1 (S330). That is, the second determination unit 944 may function as a signal generator that generates a signal (information) showing that the human subject is present on the bottom bedding M in a case in which both the first determination unit 942 and the second determination unit 944 determine that the human subject is present on the bottom bedding M. On the other hand, if it is determined that the human subject is not present on the bottom bedding M (S320: NO), the second determination unit 944 sets the present-on-bed determination flag $LF_p$ to 0 (S340). After setting the present-on-bed determination flag LF, a single present-on-bed determination process (S10) ends.

As shown in FIG. 8, if the present-on-bed determination condition is fulfilled, that is, if the present-on-bed determination flag $LF_p$ is set to 1 (S20: YES), the CPU 9 initiates a sleep measurement process (S30). On the other hand, if the present-on-bed determination condition is not fulfilled, that is, if the present-on-bed determination flag $LF_p$ is set to 0 (S20: NO), the CPU 9 repeats the present-on-bed determination process (S10). If the sleep measurement process starts, while the measurement unit 98 executes the sleep measurement process, the determination unit 94 executes a present-on-bed determination process (S40).

A present-on-bed determination process in the step S40 (S210 to S440) will be explained with reference to FIG. 22. The first determination unit 942 executes a present-on-bed determination process (S210 to S270) based on a standard deviation $\sigma_p$, which is similar to the first embodiment. If it is determined that the human subject is present on the bottom bedding M (S250: NO), the first determination unit 942 sets the present-on-bed determination flag $LF_p$ to 1 (S270) and a single present-on-bed determination process (S40) ends. On the other hand, if it is determined that the human subject is not present on the bottom bedding M (S250: YES), the first determination unit 942 generates a signal (information) showing that the human subject is not present on the bed to supply the second determination unit 944 therewith.

If the first determination unit 942 has determined that the human subject is not present on the bed, the second determination unit 944 executes a present-on-bed determination process (S410 to S440) based on frequency analysis, which is similar to the second embodiment. If it is determined that the human subject is not present on the bottom bedding M (S420: YES), the second determination unit 944 sets the present-on-bed determination flag $LF_p$ to 0 (S430). That is, the second determination unit 944 may function as a signal generator that generates a signal (information) showing that the human subject is not present on the bottom bedding M in a case in which both the first determination unit 942 and the second determination unit 944 determine that the human subject is not present on the bottom bedding M. On the other hand, if it is determined that the human subject is present on the bottom bedding M (S420: NO), the second determination unit 944 sets present-on-bed determination flag $LF_p$ to 1 (S440). After setting the present-on-bed determination flag LF, a single present-on-bed determination process (S40) ends.

Figure 23:
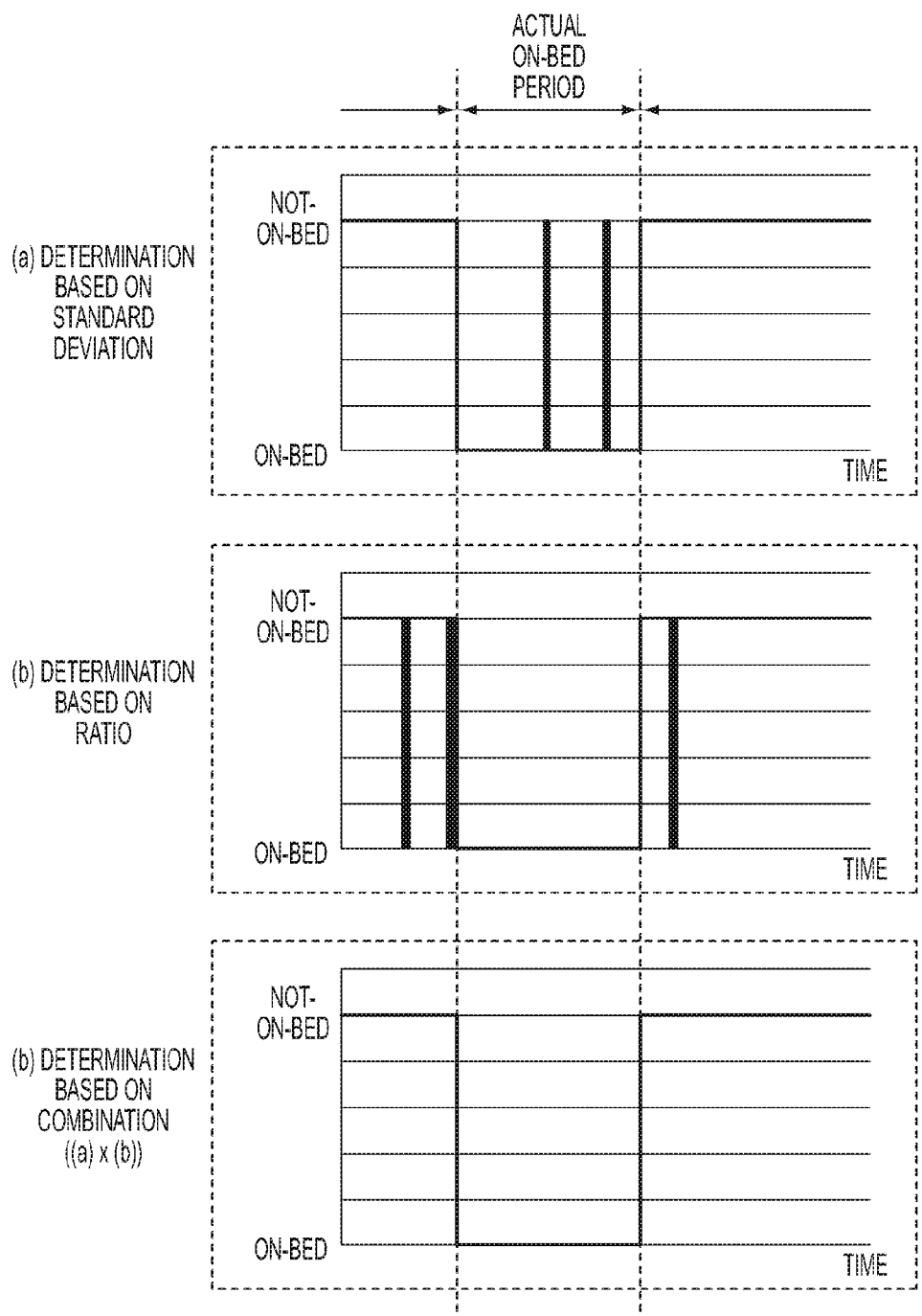
FIG. 23 illustrates an example of comparison among determination results in accordance with respective present-on-bed determinations.

With reference to FIG. 23, results of (a) the present-on-bed determination based on a standard deviation σ (executed only by the first determination unit 942), (b) the present-on-bed determination based on a ratio (executed only by the second determination unit 944), and (c) the present-on-bed determination based on combination of a standard deviation σ and a ratio according to this embodiment will be exemplified. In FIG. 23, the results obtained by executing the respective present-on-bed determinations on the first level values that show the same transition are illustrated with a common time axis for each graph. A period in which it is determined that the human subject is not present on the bed (NOT-ON-BED) is shown as a solid line in the top of each graph, and a period in which it is determined that the human subject is present on the bed (ON-BED) is shown as a solid line in the bottom of each graph.

In FIG. 23, according to (a) the present-on-bed determination based on the standard deviation σ, although the period in which the human subject is actually present on the bed and the periods in which it is determined that the human subject is present on the bed greatly overlap, there are some periods in which it is determined that the human subject is not present on the bed in spite of the actual presence of the human subject. According to (b) the present-on-bed determination based on the ratio, although the period in which the human subject is actually present on the bed and the periods in which it is determined that the human subject is present on the bed greatly overlap, there are some periods in which it is determined that the human subject is present even though the human subject is actually not present on the bed. In contrast, according to (c) the present-on-determination based on the combination of the standard deviation σ and the ratio, the period in which the human subject is actually present on the bed corresponds to the period in which it is determined that the human subject is present on the bed. As described above, the present-on-determination (c) can resolve the possible discrepancy between the period in which the human subject is actually present on the bed and the periods in which it is determined that the human subject is present on the bed in the present-on-determinations (a) and (b).

According to the above-described embodiment, it is determined whether or not the human subject is present on the bed in accordance with the combination of the present-on-bed determination results based on the standard deviation of the first level values described in the first embodiment and the present-on-bed determination result based on the frequency analysis on the first level values described in the second embodiment. As a result, more accurate present-on-bed determination results can be provided. Furthermore, similar to the first and second embodiments, it is automatically determined whether or not the human subject is present on the bed, which provides the human subject with greater convenience.

Other Variations and Modifications

The above-described embodiments can be variously modified. Some specific modifications will be exemplified hereinafter. Two or more of modifications selected from the following examples can be appropriately combined as far as no conflict occurs.

(1) Modification 1

In the above-described embodiments, the sleep measurement apparatuses are exemplified as the present-on-bed determination apparatus. However, each sleep measurement apparatus is only a non-limiting application example of the present-on-bed determination apparatus according to the present invention. For instance, the present-on-bed determination apparatus can be used by itself with a bed in a hospital or a nursing-care facility in order to determine whether or not a patient or a care-receiver is present on the bed. Furthermore, the present-on-bed determination apparatus can be applied to other apparatuses such as an alarm clock. In those cases, the present-on-bed determination apparatus does not need to include the elements used for the sleep measurement process (e.g., the second A/D conversion unit 92, the second signal processing unit 8, the biological information acquisition unit 96, the measurement unit 98, etc.).

(2) Modification 2

Figure 24:
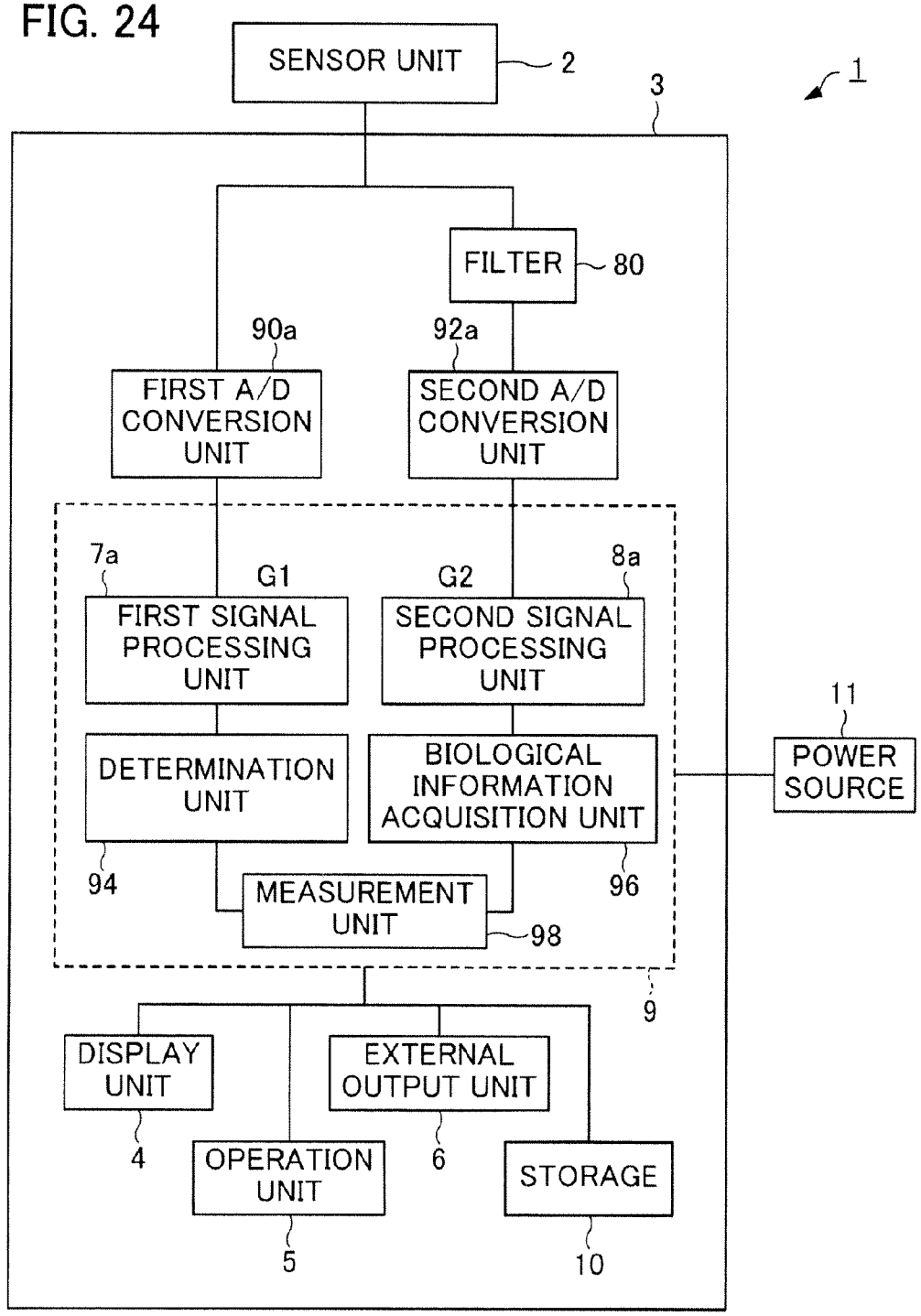
FIG. 24 is a block diagram that shows configurations of a sleep measurement apparatus according to a modification of the present invention.

In the above-described embodiments, the first A/D conversion unit 90 and the second A/D conversion unit 92 are mounted in the CPU 9. However, each A/D conversion unit may be mounted in any location. For instance, as illustrated in FIG. 24, the A/D conversion units (90a, 92a) may be mounted outside the CPU 9. In other words, whereas the amplification and the subsequent A/D conversion are applied to the measurement signal in the above-described embodiments, the A/D conversion and the subsequent amplification may be applied to the measurement signal in this modification.

In that case, the first A/D conversion unit 90a outputs a plurality of first sample values obtained by A/D conversion of the measurement signal to supply the first signal processing unit 7a therewith. The first signal processing unit 7a in the CPU 9 numerically amplifies the plurality of the first sample values with a first gain G1 so as to output a plurality of first level values to the determination unit 94. Similarly, the second A/D conversion unit 92a outputs a plurality of second sample values obtained by A/D conversion or the measurement signal to supply the second signal processing unit 8a therewith. The second signal processing unit 8a in the CPU 9 numerically amplifies the plurality of the second sample values with a second gain G2 so as to output a plurality of second level values to the biological information acquisition unit 96.

Furthermore, in this modification, only any one of the combination of the first signal processing unit 7 and the first A/D conversion unit 90 or the combination of the second signal processing unit 8 and the second A/D conversion unit 92 may be installed.

(3) Modification 3

The first A/D conversion unit 90 and the second A/D conversion unit 92 may be configured as one unit. In that case, an A/D converter with plural input ports and plural output ports can be appropriately adopted.

(4) Modification 4

In the above-described embodiments, the standard deviation σ is adopted as an indicator that indicates dispersion degree of first level values obtained during each unit period U. However, any dispersion indicator can be used. For instance, a variance of the first level values or a variation coefficient of the first level values (i.e., a value obtained by dividing a standard deviation by a mean value) can be adopted as the dispersion indicator.

(5) Modification 5

In the above-described embodiments, the respiration is adopted as a cyclic component included in biological displacement of the human subject. However, any biological displacement which changes cyclically (e.g., heartbeat) can be adopted as the cyclic component. Combination of cyclic components (e.g., respiration and heartbeat) can be adopted. In those cases, elements influencing the present-on-bed determination (e.g., a frequency characteristic of a filter in the sleep measurement apparatus 1, length of the unit period U, etc.) may be set in accordance with one or more adopted cyclic components. In particular, a filter with a frequency characteristic configured to extract a frequency component corresponding to the one or more adopted cyclic components may be mounted between the sensor unit 2 and the first amplifier 70.

(6) Modification 6

The above-described embodiments can be modified so that the CPU 9 counts elapsed time in cooperation with a real time clock (RTC). In this modification, a backup power source may supply electric power to the real time clock when the power source 11 does not supply electric power. As a result, it will be possible to continue to count elapsed time even when the power source 11 does not supply electric power. The CPU 9 and the storage 10 in the above-described embodiments may be replaced with a single microcomputer. The condenser microphone in the sensor unit 2 may be replaced with a piezoelectric element such as a piezo cable, a capacitance sensor, a photodetector, a film sensor, a strain gage, etc.

(7) Modification 7

Figure 25:
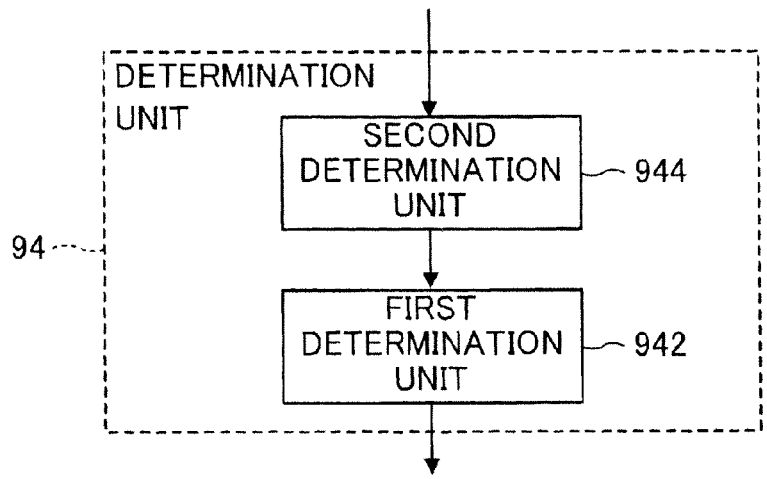
FIG. 25 illustrates a detailed configuration of a determination unit in a sleep measurement apparatus according to a modification.

In the third embodiment, the first determination unit 942 executes the present-on-bed determination based on the standard deviation σ. Subsequently, the second determination unit 944 executes the present-on-bed determination based on the frequency analysis. However, as illustrated in FIG. 25, the second determination unit 944 may execute the present-on-bed determination based on the frequency analysis first, and the first determination unit 942 may subsequently execute the present-on-bed determination based on the standard deviation σ.

In that case, in lieu of the determination operation illustrated in FIG. 21, the second determination unit 944 executes the present-on-bed determination process based on the frequency analysis corresponding to the second embodiment (S310 to S340). If it is determined that the human subject is present on the bed, the first determination unit 942 executes the present-on-bed determination process based on the standard deviation $\sigma_p$ corresponding to the first embodiment (S110 to S170). If it is determined that the human subject is present on the bed, the first determination unit 942 sets the present-on-bed determination flag $LF_p$ to 1. That is, in this modification, the first determination unit 942 may function as a signal generator that generates a signal (information) showing that the human subject is present on the bed in a case in which both the first determination unit 942 and the second determination unit 944 determine that the human subject is present on the bed.

Similarly, in lieu of the determination operation illustrated in FIG. 22, the second determination unit 944 executes the present-on-bed determination process based on the frequency analysis (S410 to S440). If it is determined that the human subject is not present on the bed, the first determination unit 942 executes the present-on-bed determination process based on the standard deviation $\sigma_p$ (S210 to S270). That is, in this modification, the first determination unit 942 may function as a signal generator that generates a signal (information) showing that the human subject is not present on the bed in a case in which both the first determination unit 942 and the second determination unit 944 determine that the human subject is not present on the bed.

Figure 26:
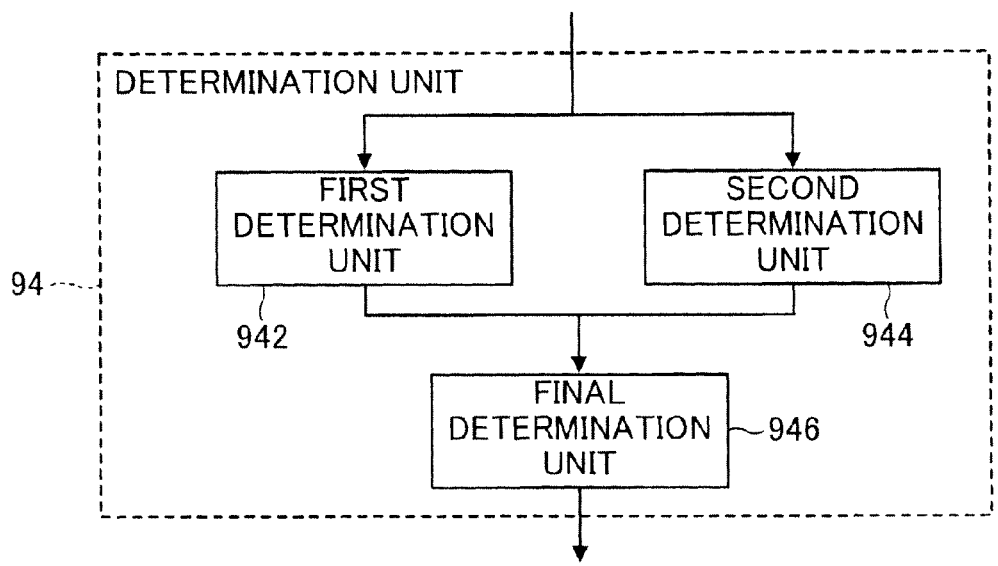
FIG. 26 illustrates a detailed configuration of a determination unit in a sleep measurement apparatus according to a modification.

Alternatively, as illustrated in FIG. 26, the first determination unit 942 and the second determination unit 944 may be mounted in parallel with each other, and both of the present-on-bed determination operations may be parallely (separately) executed. In that case, a final determination unit 946 may be mounted subsequent to the first determination unit 942 and the second determination unit 944. The final determination unit 946 may execute final determination based on the determination results of the first determination unit 942 and the second determination unit 944.

In the present-on-bed determination process of the step S10, in which it has been previously determined that the human subject is present on the bed, the final determination unit 946 determines that the human subject is present on the bottom bedding M (i.e., sets the present-on-bed determination flag $FL_p$ to 1) in a case in which both of the first determination unit 942 and the second determination unit 944 determine that the human subject is present on the bottom bedding M.

On the other hand, in the present-on-bed determination process of the step S40, in which it has been previously determined that the human subject is not present on the bed, the final determination unit 946 determines that the human subject is not present on the bottom bedding M (i.e., sets the present-on-bed determination flag $FL_p$ to 0) in a case in which both of the first determination unit 942 and the second determination unit 944 determine that the human subject is not present on the bottom bedding M.

That is, the final determination unit 946 may function as the signal generator described in the third embodiment.

In summary, the present-on-bed determination based on the standard deviation σ and the present-on-bed determination based on the frequency analysis may be executed in any order.

(8) Modification 8

In the second and third embodiments, the ratio of the noise component (first component) to the biosignal component (second component) (i.e., $(LC_p+HC_p)/MC_p$) is used for the present-on-bed determination. However, a ratio of the biosignal component to the noise component (i.e., $MC_p/(LC_p+HC_p)$) may be used for the present-on-bed determination. The ratio of this modification becomes greater when the biosignal component becomes larger relative to the noise component, since the numerator of the ratio is the biosignal component and the denominator of the ratio is the noise component. When the ratio of this modification is used for the present-on-bed deter urination, on each determination step (S320, S420), determination with reversing the inequality sign (i.e., determination whether or not the ratio exceeds the fourth threshold Th4 on the step S320, and determination whether or not the ratio is less than the fifth threshold Th5 on the step S420) may be executed. As a result, present-on-bed determination equivalent to the present-on-bed determination according to the second or third embodiment can be provided.

(9) Modification 9

In the second and third embodiments, the noise component (first component) is a sum of the component value $LC_p$ of the low-frequency range and the component value $HC_p$ of the high-frequency range (i.e., $LC_p+HC_p$). However, the noise component (first component) may be any one of the component value $LC_p$ of the low-frequency range or the component value $HC_p$ of the high-frequency range.

What is claimed is:

1. A present-on-bed determination apparatus comprising:
a sensor unit usable with a bottom bedding and configured to measure biological displacement of a human subject on the bottom bedding so as to output a measurement signal indicating a measurement result;
a first signal processing unit configured to amplify the measurement signal with a first gain so as to output a first output signal;
a first A/D conversion unit configured to output a plurality of first level values obtained by A/D conversion of the first output signal; and
a determination unit configured to determine whether or not the human subject is present on the bottom bedding in accordance with a dispersion indicator that indicates dispersion degree of the plurality of the first level values,
wherein the first gain is set so that a period during which the first level value stays at a maximum attainable value and a period during which the first value stays at a minimum attainable value are included in one cycle of a periodic component contained in the biological displacement of the human subject present on the bottom bedding.

2. A present-on-bed determination apparatus comprising:
a sensor unit usable with a bottom bedding and configured to measure biological displacement of a human subject on the bottom bedding so as to output a measurement signal indicating a measurement result;
a first A/D conversion unit configured to output a plurality of first sample values obtained by A/D conversion of the measurement signal;
a first signal processing unit configured to numerically amplify the plurality of the first sample values with a first gain so as to output a plurality of first level values; and
a determination unit configured to determine whether or not the human subject is present on the bottom bedding in accordance with a dispersion indicator that indicates dispersion degree of the plurality of the first level values,
wherein the first gain is set so that a period during which the first level value stays at a maximum attainable value and a period during which the first value stays at a minimum attainable value are included in one cycle of a periodic component contained in the biological displacement of the human subject present on the bottom bedding.

3. The present-on-bed determination apparatus according to claim 1 or claim 2, wherein the determination unit determines that a preliminary condition is fulfilled if the dispersion indicator of the plurality of the first level values obtained during a predetermined period exceeds a first threshold or is equal to 0, and determines that the human subject is present on the bottom bedding if a number of cases in which the preliminary condition is fulfilled in n consecutive predetermined periods is equal to or greater than a second threshold, n being a natural number equal to or greater than 2.

4. The present-on-bed determination apparatus according to claim 3, wherein, after it is determined that the human subject is present on the bottom bedding, the determination unit determines that the human subject is not present on the bottom bedding if a number of cases in which the preliminary condition is fulfilled in m consecutive predetermined periods is equal to or less than a third threshold, m being a natural number equal to or greater than 2, the third threshold being smaller than the second threshold.

5. The present-on-bed determination apparatus according to claim 3, wherein each time length of the predetermined periods is set longer than a time length required for the one cycle of the periodic component.

6. The present-on-bed determination apparatus according to claim 3, wherein the dispersion indicator is a standard deviation, a variance, or a variation coefficient of the plurality of the first level values obtained during the predetermined period.

7. A present-on-bed determination apparatus comprising:
a sensor unit usable with a bottom bedding and configured to measure biological displacement of a human subject on the bottom bedding so as to output a measurement signal indicating a measurement result;
a first signal processing unit configured to amplify the measurement signal with a first gain so as to output a first output signal;
a first A/D conversion unit configured to output a plurality of first level values obtained by A/D conversion of the first output signal; and
a determination unit configured to execute frequency analysis on the plurality of the first level values output during an analysis period to obtain a first component not derived from the biological displacement of the human subject and a second component derived from the biological displacement of the human subject, and configured to determine whether or not the human subject is present on the bottom bedding in accordance with a ratio between the first component and the second component,
wherein the first gain is set so that a period during which the first level value stays at a maximum attainable value and a period during which the first value stays at a minimum attainable value are included in one cycle of a periodic component contained in the biological displacement of the human subject present on the bottom bedding.

8. A present-on-bed determination apparatus comprising:
a sensor unit usable with a bottom bedding and configured to measure biological displacement of a human subject on the bottom bedding so as to output a measurement signal indicating a measurement result;
a first A/D conversion unit configured to output a plurality of first sample values obtained by A/D conversion of the measurement signal;
a first signal processing unit configured to numerically amplify the plurality of the first sample values with a first gain so as to output a plurality of first level values; and
a determination unit configured to execute frequency analysis on the plurality of the first level values output during an analysis period to obtain a first component not derived from the biological displacement of the human subject and a second component derived from the biological displacement of the human subject, and configured to determine whether or not the human subject is present on the bottom bedding in accordance with a ratio between the first component and the second component,
wherein the first gain is set so that a period during which the first level value stays at a maximum attainable value and a period during which the first value stays at a minimum attainable value are included in one cycle of a periodic component contained in the biological displacement of the human subject present on the bottom bedding.

9. The present-on-bed determination apparatus according to claim 7 or claim 8, wherein the determination unit obtains any one or both of a component less than a first frequency and a component greater than a second frequency that exceeds the first frequency as the first component, and obtains a component equal to or greater than the first frequency and equal to or less than the second frequency as the second component.

10. The present-on-bed determination apparatus according to claim 9, wherein the ratio represents a ratio of the first component to the second component, and wherein the determination unit determines that the human subject is present on the bottom bedding if the ratio obtained during the analysis period is less than a fourth threshold.

11. The present-on-bed determination apparatus according to claim 10, wherein, after it is determined that the human subject is present on the bottom bedding, the determination unit determines that the human subject is not present on the bottom bedding if the ratio obtained during an analysis period is greater than a fifth threshold, the fifth threshold being different from the fourth threshold.

12. The present-on-bed determination apparatus according to claim 9, wherein the ratio represents a ratio of the second component to the first component, and wherein the determination unit determines that the human subject is present on the bottom bedding if the ratio obtained during the analysis period is greater than a fourth threshold.

13. The present-on-bed determination apparatus according to claim 12, wherein, after it is determined that the human subject is present on the bottom bedding, the determination unit determines that the human subject is not present on the bottom bedding if the ratio obtained during an analysis period is less than a fifth threshold, the fifth threshold being different from the fourth threshold.

14. A present-on-bed determination apparatus comprising:
a sensor unit usable with a bottom bedding and configured to measure biological displacement of a human subject on the bottom bedding so as to output a measurement signal indicating a measurement result;
a first signal processing unit configured to amplify the measurement signal with a first gain so as to output a first output signal;
a first A/D conversion unit configured to output a plurality of first level values obtained by A/D conversion of the first output signal;
a first determination unit configured to determine whether or not the human subject is present on the bottom bedding in accordance with a dispersion indicator that indicates dispersion degree of the plurality of the first level values; and
a second determination unit configured to execute frequency analysis on the plurality of the first level values output during an analysis period to obtain a first component not derived from the biological displacement of the human subject and a second component derived from the biological displacement of the human subject, and configured to determine whether or not the human subject is present on the bottom bedding in accordance with a ratio between the first component and the second component,
wherein the first gain is set so that a period during which the first level value stays at a maximum attainable value and a period during which the first value stays at a minimum attainable value are included in one cycle of a periodic component contained in the biological displacement of the human subject present on the bottom bedding.

15. A present-on-bed determination apparatus comprising:
a sensor unit usable with a bottom bedding and configured to measure biological displacement of a human subject on the bottom bedding so as to output a measurement signal indicating a measurement result;
a first A/D conversion unit configured to output a plurality of first sample values obtained by A/D conversion of the measurement signal;
a first signal processing unit configured to numerically amplify the plurality of the first sample values with a first gain so as to output a plurality of first level values;
a first determination unit configured to determine whether or not the human subject is present on the bottom bedding in accordance with a dispersion indicator that indicates dispersion degree of the plurality of the first level values; and a second determination unit configured to execute frequency analysis on the plurality of the first level values output during an analysis period to obtain a first component not derived from the biological displacement of the human subject and a second component derived from the biological displacement of the human subject, and configured to determine whether or not the human subject is present on the bottom bedding in accordance with a ratio between the first component and the second component, wherein the first gain is set so that a period during which the first level value stays at a maximum attainable value and a period during which the first value stays at a minimum attainable value are included in one cycle of a periodic component contained in the biological displacement of the human subject present on the bottom bedding.

16. The present-on-bed determination apparatus according to claim 14 or claim 15, wherein the second determination unit obtains any one or both of a component less than a first frequency and a component greater than a second frequency that exceeds the first frequency as the first component, and obtains a component equal to or greater than the first frequency and equal to or less than the second frequency as the second component.

17. The present-on-bed determination apparatus according to claim 16, further comprising a signal generator, wherein the first determination unit determines that a preliminary condition is fulfilled if the dispersion indicator of the plurality of the first level values obtained during a predetermined period exceeds a first threshold or is equal to 0, and determines that the human subject is present on the bottom bedding if a number of cases in which the preliminary condition is fulfilled in n consecutive predetermined periods is equal to or greater than a second threshold, n being a natural number equal to or greater than 2, wherein the ratio represents a ratio of the first component to the second component, wherein the second determination unit determines that the human subject is present on the bottom bedding if the ratio obtained during the analysis period is less than a fourth threshold, and wherein the signal generator generates a signal indicating that the human subject is present on the bottom bedding in a case in which both the first determination unit and the second determination unit determine that the human subject is present on the bottom bedding.

18. The present-on-bed determination apparatus according to claim 17, wherein, after the second determination unit determines that the human subject is present on the bottom bedding, the first determination unit determines that the human subject is not present on the bottom bedding if a number of cases in which the preliminary condition is fulfilled in m consecutive predetermined periods is equal to or less than a third threshold, m being a natural number equal to or greater than 2, the third threshold being smaller than the second threshold, wherein the second determination unit determines that the human subject is not present on the bottom bedding if the ratio obtained during an analysis period is greater than a fifth threshold, the fifth threshold being different from the fourth threshold, and wherein the signal generator generates a signal indicating that the human subject is not present on the bottom bedding in a case in which both the first determination unit and the second determination unit determine that the human subject is not present on the bottom bedding.

19. The present-on-bed determination apparatus according to claim 17, wherein each time length of the predetermined periods is set longer than a time length required for the one cycle of the periodic component.

20. The present-on-bed determination apparatus according to claim 17, wherein the dispersion indicator is a standard deviation, a variance, or a variation coefficient of the plurality of the first level values obtained during the predetermined period.

21. The present-on-bed determination apparatus according to claim 16, further comprising a signal generator, wherein the first determination unit determines that a preliminary condition is fulfilled if the dispersion indicator of the plurality of the first level values obtained during a predetermined period exceeds a first threshold or is equal to 0, and determines that the human subject is present on the bottom bedding if a number of cases in which the preliminary condition is fulfilled in n consecutive predetermined periods is equal to or greater than a second threshold, n being a natural number equal to or greater than 2, wherein the ratio represents a ratio of the second component to the first component, wherein the second determination unit determines that the human subject is present on the bottom bedding if the ratio obtained during the analysis period is greater than a fourth threshold, and wherein the signal generator generates a signal indicating that the human subject is present on the bottom bedding in a case in which both the first determination unit and the second determination unit determine that the human subject is present on the bottom bedding.

22. The present-on-bed determination apparatus according to claim 21, wherein, after the second determination unit determines that the human subject is present on the bottom bedding, the first determination unit determines that the human subject is not present on the bottom bedding if a number of cases in which the preliminary condition is fulfilled in m consecutive predetermined periods is equal to or less than a third threshold, m being a natural number equal to or greater than 2, the third threshold being smaller than the second threshold, wherein the second determination unit determines that the human subject is not present on the bottom bedding if the ratio obtained during an analysis period is less than a fifth threshold, the fifth threshold being different from the fourth threshold, and wherein the signal generator generates a signal indicating that the human subject is not present on the bottom bedding in a case in which both the first determination unit and the second determination unit determine that the human subject is not present on the bottom bedding.

23. The present-on-bed determination apparatus according to claim 21, wherein each time length of the predetermined periods is set longer than a time length required for the one cycle of the periodic component.

24. The present-on-bed determination apparatus according to claim 21, wherein the dispersion indicator is a standard deviation, a variance, or a variation coefficient of the plurality of the first level values obtained during the predetermined period.

25. A sleep measurement apparatus comprising:
the present-on-bed determination apparatus according to any one of claims 1, 2, 7, 8, 14, and 15,
wherein the present-on-bed determination apparatus further comprises:
  a second signal processing unit;
  a second A/D conversion unit;
  a biological information acquisition unit; and
  a measurement unit,
wherein in a case in which it is determined that the human subject is present on the bottom bedding,
the second signal processing unit amplifies the measurement signal with a second gain less than the first gain so as to output a second output signal,
the second A/D conversion unit outputs a plurality of second level values obtained by A/D conversion of the second output signal,
the biological information acquisition unit obtains biological information of the human subject based on the second level values to output the biological information, and
the measurement unit measures sleeping conditions of the human subject based on the biological information.

26. A sleep measurement apparatus comprising:
the present-on-bed determination apparatus according to any one of claims 1, 2, 7, 8, 14, and 15,
wherein the present-on-bed determination apparatus further comprises:
  a second A/D conversion unit;
  a second signal processing unit;
  a biological information acquisition unit; and
  a measurement unit,
wherein in a case in which it is determined that be human subject is present on the bottom bedding,
the second A/D conversion unit outputs a plurality of second sample values obtained by A/D conversion of the measurement signal,
the second signal processing unit numerically amplifies the plurality of the second sample values with a second gain less than the first gain so as to output a plurality of second level values,
the biological information acquisition unit obtains biological information of the human subject based on the second level values to output the biological information, and
the measurement unit measures sleeping conditions of the human subject based on the biological information.

* * * * *